United States Patent
Sei et al.

(10) Patent No.: US 11,733,142 B2
(45) Date of Patent: Aug. 22, 2023

(54) ANTIMICROBIC SUSCEPTIBILITY TESTING USING DIGITAL MICROSCOPY

(71) Applicant: Beckman Coulter, Inc., Brea, CA (US)

(72) Inventors: Katherine Sei, El Dorado, CA (US); David Lewis, Fairfield, CA (US)

(73) Assignee: BECKMAN COULTER, INC., Brea, CA (US)

( * ) Notice: Subject to any disclaimer, the term of this patent is extended or adjusted under 35 U.S.C. 154(b) by 825 days.

(21) Appl. No.: 16/479,804

(22) PCT Filed: Jan. 22, 2018

(86) PCT No.: PCT/US2018/014660
§ 371 (c)(1),
(2) Date: Jul. 22, 2019

(87) PCT Pub. No.: WO2018/136864
PCT Pub. Date: Jul. 26, 2018

(65) Prior Publication Data
US 2021/0041338 A1 Feb. 11, 2021

Related U.S. Application Data

(60) Provisional application No. 62/449,373, filed on Jan. 23, 2017, provisional application No. 62/574,795, filed on Oct. 20, 2017.

(51) Int. Cl.
*G06T 7/62* (2017.01)
*G01N 15/06* (2006.01)
(Continued)

(52) U.S. Cl.
CPC .............. *G01N 15/06* (2013.01); *C12M 41/14* (2013.01); *C12M 41/36* (2013.01); *C12Q 1/18* (2013.01);
(Continued)

(58) Field of Classification Search
CPC ......... C12M 41/14; C12M 41/36; C12Q 1/18; G01N 15/0227; G01N 15/06;
(Continued)

(56) References Cited

U.S. PATENT DOCUMENTS

| | | | | |
|---|---|---|---|---|
| 4,453,220 A | * | 6/1984 | Flegal | G16H 40/40 702/19 |
| 4,720,463 A | * | 1/1988 | Farber | G01N 35/00 414/331.14 |

(Continued)

FOREIGN PATENT DOCUMENTS

| | | | | |
|---|---|---|---|---|
| EP | 1236513 A1 | * | 9/2002 | ........ B01L 3/502707 |
| WO | WO 2000/055357 A1 | | 9/2000 | |

OTHER PUBLICATIONS

Peach, Kelly C., et al. "Mechanism of action-based classification of antibiotics using high-content bacterial image analysis." *Molecular BioSystems* 9.7 (2013): 1837-1848.
(Continued)

*Primary Examiner* — Tsung Yin Tsai
(74) *Attorney, Agent, or Firm* — Frost Brown Todd LLP

(57) ABSTRACT

An optimized testing method is used to determine minimum inhibitory concentration (MIC) of a particular antimicrobic for use with a particular microbe. The testing method includes iteratively imaging the microbes mixed with various concentrations of the antimicrobic. The images are thereafter processed to determine one or more of the amount/count of the microbes in each image, the total area occupied by the microbes in each image, and the ratio between the area occupied by the microbes and the count of the microbes. Once a sufficient amount of data is collected, the MIC is determined based on one or more of the count, area, and ratio datasets.

17 Claims, 27 Drawing Sheets

(51) Int. Cl.
  *G06T 7/136* (2017.01)
  *C12M 1/00* (2006.01)
  *C12M 1/34* (2006.01)
  *C12Q 1/18* (2006.01)
  *G01N 15/02* (2006.01)
  *G06T 5/00* (2006.01)
  *G06T 7/00* (2017.01)

(52) U.S. Cl.
  CPC ......... *G01N 15/0227* (2013.01); *G06T 5/002* (2013.01); *G06T 7/0012* (2013.01); *G06T 7/136* (2017.01); *G06T 7/62* (2017.01); *G01N 2015/0693* (2013.01); *G06T 2207/10056* (2013.01); *G06T 2207/30024* (2013.01); *G06T 2207/30242* (2013.01)

(58) Field of Classification Search
  CPC ....... G01N 15/1475; G01N 2015/0693; G01N 2015/1006; G01N 2015/1486; G06T 2207/10056; G06T 2207/30024; G06T 2207/30242; G06T 5/002; G06T 7/0012; G06T 7/136; G06T 7/62
  See application file for complete search history.

(56) References Cited

U.S. PATENT DOCUMENTS

| | | | | |
|---|---|---|---|---|
| 4,724,215 A | * | 2/1988 | Farber | G01N 35/00 348/82 |
| 4,856,073 A | * | 8/1989 | Farber | G01N 35/00 382/128 |
| 4,928,269 A | * | 5/1990 | Kimball | G01V 1/306 181/105 |
| 6,573,088 B2 | * | 6/2003 | Gemmell | G01N 35/0092 422/65 |
| 6,632,654 B1 | * | 10/2003 | Gebrian | G01N 35/00029 422/561 |
| 6,645,737 B2 | * | 11/2003 | Farina | C12Q 1/18 435/288.5 |
| 2002/0119561 A1 | * | 8/2002 | Farina | B01L 3/502723 435/288.5 |
| 2002/0155515 A1 | * | 10/2002 | Farina | C12Q 1/18 435/32 |
| 2002/0155590 A1 | * | 10/2002 | Gebrian | G01N 35/1002 422/63 |
| 2003/0031601 A1 | * | 2/2003 | Gebrian | B01F 33/30 422/561 |
| 2003/0032171 A1 | * | 2/2003 | Gemmell | G01N 35/025 435/286.2 |
| 2003/0032173 A1 | * | 2/2003 | Farina | B01F 33/452 422/547 |
| 2005/0009032 A1 | * | 1/2005 | Coleman | G06T 7/0012 382/128 |
| 2012/0088691 A1 | * | 4/2012 | Chen | C12Q 1/6851 435/6.12 |
| 2014/0126802 A1 | | 5/2014 | Adiga et al. | |

OTHER PUBLICATIONS

International Search Report and Written Opinion dated Mar. 19, 2018 for International Application No. PCT/US2018/014660, 9 pages.

* cited by examiner

ANTIMICROBIC SUSCEPTIBILITY TESTING USING DIGITAL MICROSCOPY

CROSS-REFERENCE TO RELATED APPLICATIONS

This application claims the benefit of U.S. Provisional Application No. 62/574,795, filed on Oct. 20, 2017 and U.S. Provisional Application No. 62/449,373, filed on Jan. 23, 2017.

BACKGROUND

Various types of tests related to patient diagnosis and therapy can be performed by analysis of the patient's microorganisms, or "microbes." Microbes are microscopic living organisms such as bacteria, fungi, or viruses, which may be single-celled or multicellular. Biological samples containing the patient's microorganisms may be taken from a patient's infections, bodily fluids or abscesses and may be placed in test panels or arrays, combined with various reagents, incubated, and analyzed to aid in treatment of the patient. Automated biochemical analyzers have been developed to meet the needs of health care facilities and other institutions to facilitate analysis of patient samples and to improve the accuracy and reliability of assay results when compared to analysis using manual operations and aid in determining effectiveness of various antimicrobials. An antimicrobial is an agent that kills microorganisms or inhibits their growth, such as antibiotics which are used against bacteria and antifungals which are used against fungi. However, with ever changing bacterial genera and newly discovered antimicrobials, the demand for biochemical testing has increased in both complexity and in volume.

An important family of automated microbiological analyzers function as a diagnostic tool for determining both the identity of an infecting microorganism and of an antimicrobic effective in controlling growth of the microorganism. Microbial growth is an increase in cell number, rather than cell size. For example, microbial growth in bacteria is provided through binary fission, where the cell divides from one cell into two daughter cells. No growth results when the binary fission is inhibited through some environmental factor such as temperature or lack of nutrients.

Automated microbiological analyzers function as a diagnostic tool for determining both the identity of an infecting microorganism and of an antimicrobic effective in controlling growth of the microorganism. In performing the diagnostic tests, identification and in vitro antimicrobic susceptibility patterns of microorganisms isolated from biological samples are ascertained. Conventional versions of such analyzers may place a small sample to be tested into a plurality of small sample test wells in panels or arrays that contain different enzyme substrates or antimicrobics in serial dilutions. Identification (ID) testing of microorganisms, and antimicrobic susceptibility testing (AST) for determining Minimum Inhibitory Concentrations (MIC) of an antimicrobic effective against the microorganism may utilize color changes, fluorescence changes, the degree of cloudiness (turbidity) in the sample test wells created in the arrays, or other information derived from the testing. Both AST and ID measurements and subsequent analysis may be performed by computer controlled microbiological analyzers to provide advantages in reproducibility, reduction in processing time, avoidance of transcription errors and standardization for all tests run in the laboratory.

In ID testing of a microorganism, a standardized dilution of the patient's microorganism sample, known as an inoculum, is first prepared in order to provide a bacterial or cellular suspension having a predetermined known concentration. This inoculum is placed in a plurality of test wells that may contain or thereafter be supplied with predetermined test media. Depending on the species of microorganism present, this media will facilitate changes in color, turbidity, fluorescence, or other characteristics after incubation. These changes are used to identify the microorganism in ID testing.

In AST testing, a plurality of test wells are filled with inoculum and an increasing concentrations of a number of different antimicrobial agents, for example antibiotics. The different antimicrobial agents may be diluted in a growth medium or liquid medium to concentrations that include those of clinical interest. After incubation, the turbidity will be increased or unchanged in test wells where growth has not been inhibited by the antimicrobics in those test wells. The MIC of each antimicrobial agent is measured by lack of growth with respect to each concentration of antimicrobial agent. It follows that the lowest concentration of antimicrobial agent displaying a lack of growth is the MIC.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
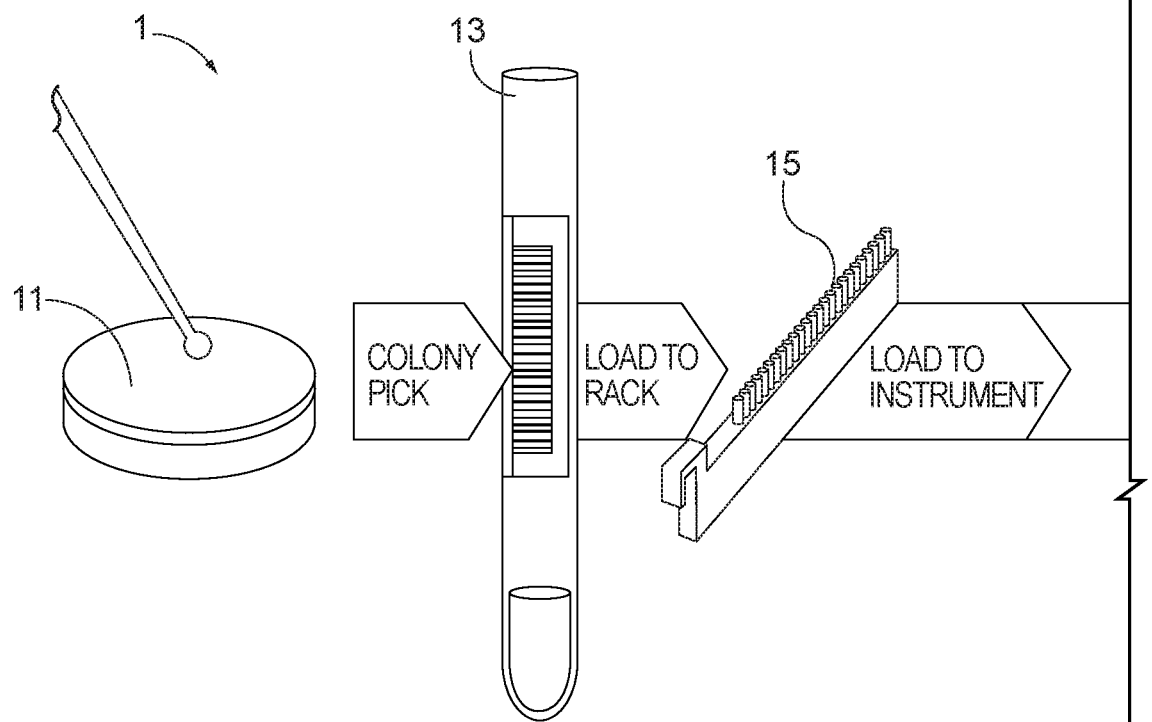
FIG. 1A depicts a portion of a diagrammatic view of an exemplary biological testing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. BIOLOGICAL TESTING SYSTEM HARDWARE

Figure 1B:
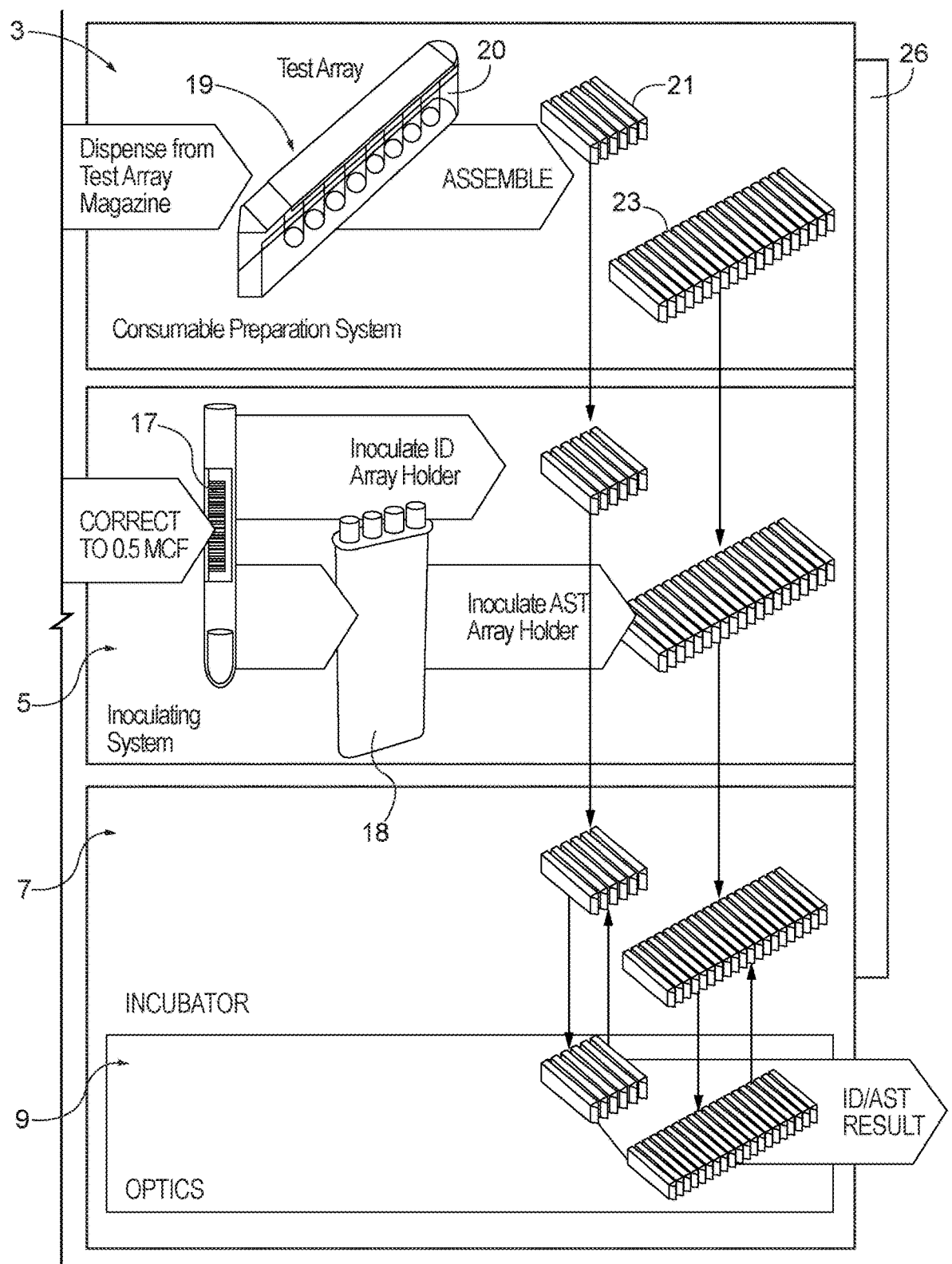
FIG. 1B depicts another portion of the diagrammatic view of the biological testing system of FIG. 1A.
Figure 19:
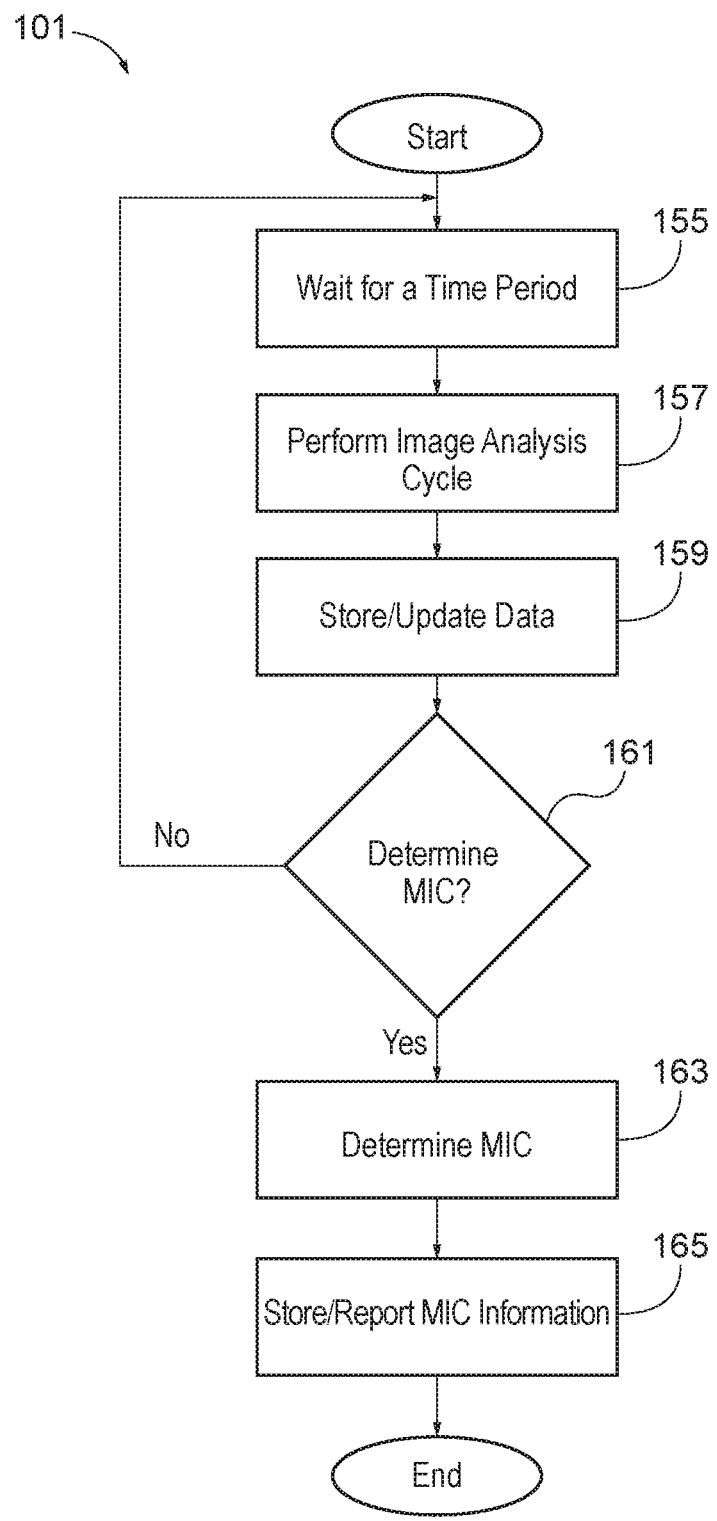
FIG. 19 depicts an exemplary optimized antimicrobic susceptibility testing method of the present invention.

FIGS. 1A and 1B depict a diagrammatical example of various hardware components available in a biological testing system 1. Biological testing system 1 facilitates an optimized antimicrobial susceptibility testing (AST) method 101 (FIG. 19). Biological testing system 1 broadly includes a consumable preparation system 3, an inoculating system 5, an incubator system 7, and an optics system 9. The various systems within biological testing system 1 coordinate with each other and work automatically once loaded with adequate material by a user.

To operate biological testing system 1, the user first acquires an appropriate microbe sample. As shown in FIG. 1A, a microbe sample may be obtained from an agar plate 11 or under certain circumstances, a blood sample may be used. Next, the user prepares an inoculum suspension by transferring the microbes into a tube containing a suitable liquid medium or broth. One such tube is shown in FIG. 1A as an inoculum 13. In some versions of biological testing system 1, the liquid medium or broth may be an approximately 0.5 mM phosphate buffered solution with small amounts of sodium and potassium chloride to aid in maintaining the viability of the microbes introduced into solution without adversely interfering with the MIC determination or other associated testing. The phosphate buffered solution may be used in both ID testing and AST testing to minimize the need for different inoculum across the two systems and leverage the efficiencies in having a single broth. Each inoculum 13 is placed into an inoculum rack 15 and the entire inoculum rack 15 is placed into inoculating system 5. Once in inoculating system 5, the inoculum in each inoculum 13 is adjusted if necessary to a standard turbidity value of 0.5 McFarland to create an inoculum 17. In some versions of biological testing system 1, a 1 microliter plastic loop or swab may be provided to the user to easily pick colonies from the agar plate and to minimize the amount of adjustment needed to bring the inoculum to the desired turbidity value. Once adjusted to the desired turbidity value, the inoculum is finalized. The finalized inoculum will be referred to hereinafter as inoculum 17, as depicted in FIG. 1B. Inoculum 17 may be further diluted into a 1:250 dilution and converted into an inoculum 18. As will be discussed in more detail below, the inoculum contained in each inoculum 17 is applied to an identification (ID) array holder 21, while the inoculum contained in each inoculum 18 is applied to an AST array holder 23. Both ID array holder 21 and AST array holder 23 are assembled by consumable preparation system 3 and provided to inoculating system 5 for use with inoculum 17 and inoculum 18.

Consumable preparation system 3 is loaded with magazines of test arrays 19, which may contain various antimicrobials or other agents required by biological testing system 1 disposed in a series of test wells 20. For example, test array 19 may comprise a antimicrobic dilution array or an identification array. Consumable preparation system 3 may also be loaded with bulk diluents (not shown) and/or various other elements for preparing and finalizing ID array holder 21 and AST array holder 23 and the inoculate therein. Primarily, consumable preparation system 3 operates to retrieve test arrays 19 as required and combine each retrieved test array 19 into either ID array holder 21 or AST array holder 23. Test arrays 19 may be selected and assembled by a robotic gripper (not shown) or other mechanical features as dictated by the prescribed testing. For example, a physician may order biological testing using the antibiotic amoxicillin. Test arrays 19 relating to amoxicillin testing are therefore retrieved and assembled into the appropriate ID array holder 21 and AST array holder 23. All or some portions of test array 19 may be formed of a styrene material to aid in reducing fluorescent crosstalk, fallout, and/or bubbles when digitally examining each test well 20. It has been found that a test array 19 formed of a styrene material is adequate for rehydration and does not require a corona treatment to prevent inoculum or diluents from flaking out of test wells 20.

Once inoculum 17, inoculum 18, ID array holder 21, and AST array holder 23 are assembled, inoculating system 5 dispenses the generally undiluted inoculum from inoculum 17 into test wells 20 of ID array holder 21 and the diluted inoculum from inoculum 18 into test wells 20 of AST array holder 23. The time between applying inoculum 17 to ID array holder 21 or inoculum 18 to AST array holder 23 and the start of logarithmic growth of the microbes disposed therein is known as "lag time." Lag time may be decreased by using enhanced broth such as a broth with yeast extract, vitamins, and/or minerals. Lag time may also be decreased by increasing the inoculum. In some versions of biological testing system 1, the amount of inoculum may be doubled to decrease the lag time by approximately 30 minutes without affecting the accuracy of the MIC determination. The dispensing may be accomplished via an elevator assembly 26 having an XY robot or XYZ robot (not shown) with a gripper (not shown) and pipettor (not shown), along with various circuitry, channels, and tubing as necessary. The XYZ robot is tasked with retrieving inoculum from inoculum racks 15 and dispensing the inoculum into test wells 20 of ID array holder 21 and AST array holder 23. Once ID array holder 21 and AST array holder 23 are sufficiently loaded with inoculum, each ID array holder 21 and AST array holder 23 are moved into incubator system 7 by way of an elevator assembly 26.

Figure 2:
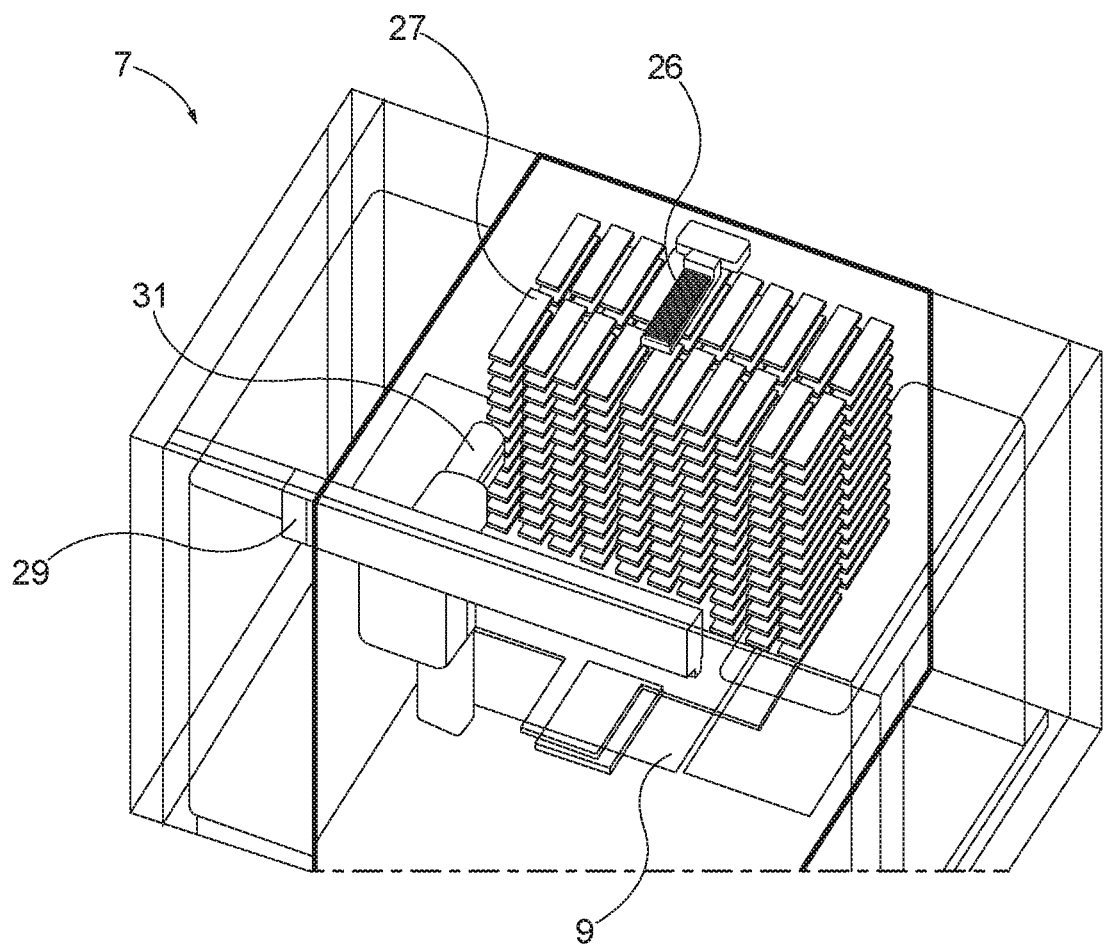
FIG. 2 depicts a perspective view of an exemplary incubator system and an exemplary optics system of the biological testing system of FIG. 1B.

As shown in FIG. 2, incubator system 7 includes slots 27 for holding a large number of ID array holders 21 and AST array holders 23. Each array holder is placed into a corresponding slot 27 by an XYZ robot 29 using a gripper 31. XYZ robot 29 operates to move in any portion of the XYZ plane and position gripper 31 proximate the desired ID array holder 21 or AST array holder 23. While in incubator system 7, each array holder incubates in specific desired environmental conditions. For example, incubator system 7 may be set to incubate array holders at thirty-five degrees Celsius. At certain time intervals during the incubation, XYZ robot 29 retrieves a particular ID array holder 21 or AST array holder 23 and move the selected array holder into the optics system 9.

Figure 3:
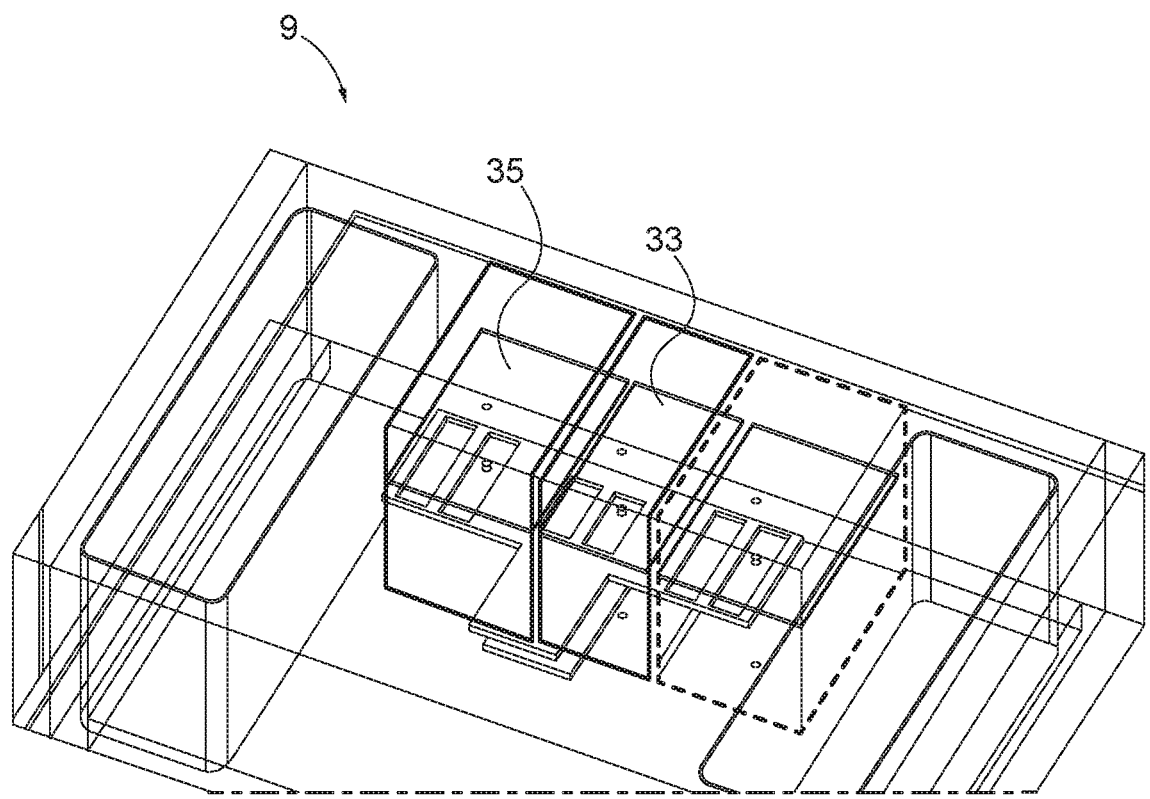
FIG. 3 depicts a perspective view of the optics system of FIG. 2.
Figure 4:
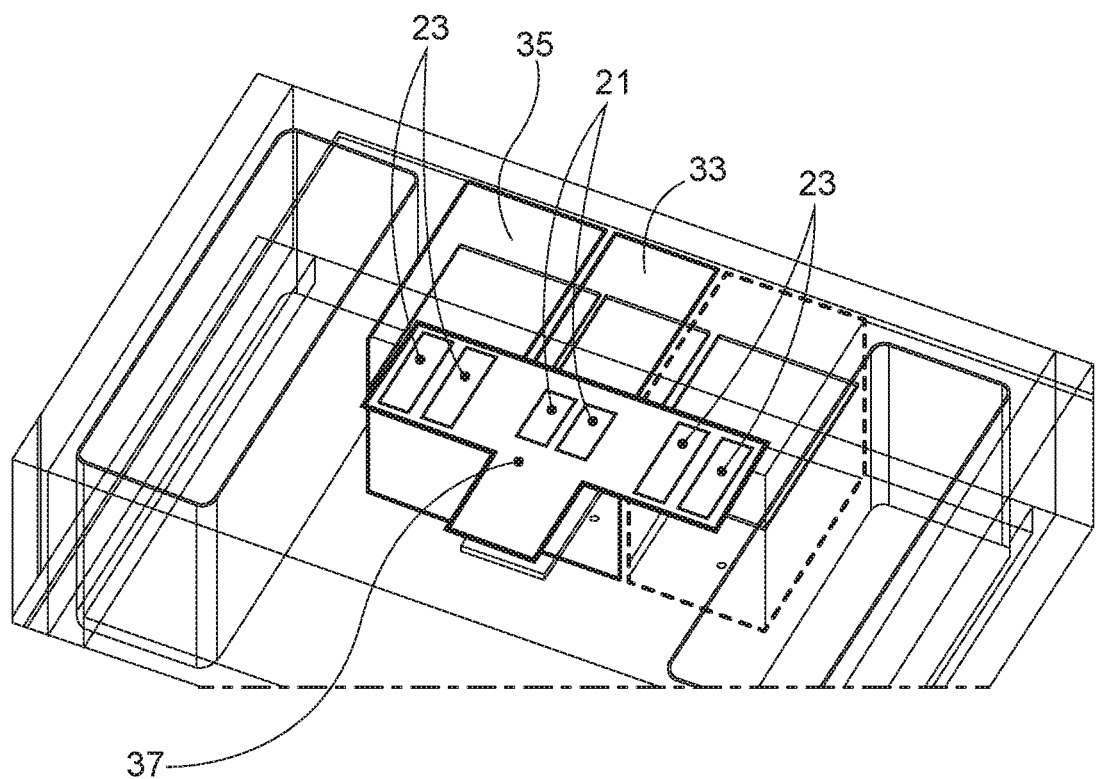
FIG. 4 depicts another perspective view of the optics system of FIG. 2 showing an XY stage of the optics system.

As shown in FIG. 2-4, optics system 9 includes features that are configured to observe, monitor, review, and/or capture images for each test well 20 of an ID array holder 21 or AST array holder 23. Specifically, each ID array holder 21 is monitored by an ID fluorimeter 33, which each AST array holder 23 is monitored by an AST camera 35. To accomplish the monitoring, XYZ robot 29 retrieves the particular array holder with gripper 31 and places the selected array holder onto an XY-stage 37. The XY-stage 37 moves in the XY plane to position the array holder under the associated monitoring element, namely, the ID array holders 21 are disposed under the ID fluorimeter 33 and the AST array holders 23 are disposed under the AST camera 35 for monitoring and observation in optics system 9. XY-stage 37 includes finely tuned motor control to allow each test well 20 of the associated array holder to be positioned accurately within the observation frame of either ID fluorimeter 33 or AST camera 35.

Figure 5:
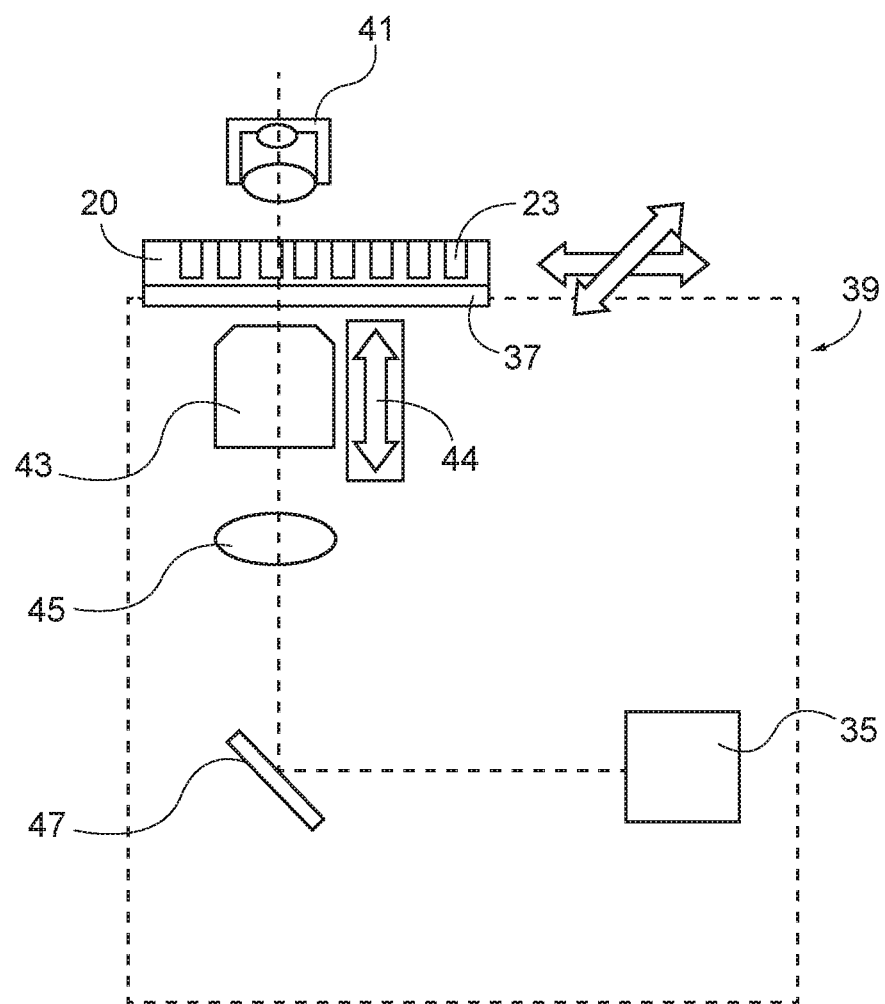
FIG. 5 depicts a diagrammatic view of portions of the optics system of FIG. 2.

FIG. 5 illustrates an exemplary architecture for an AST optics portion 39 of optics system 9. AST optics portion 39 includes an illumination source 41, an objective lens 43, a tube lens 45, and a fold mirror 47. Illumination source 41 may comprise a condenser LED system for providing monochromatic illumination of each test well 20 of AST array holder 23. Objective lens 43 may comprise a Nikon 20× 0.45NA ELWD objective lens or any other suitable kind of lens. Objective lens 43 may comprise a 20× objective lens with each pixel covering about 0.33 microns. A 20× objective lens provides both the ability to detect a reasonable number of cells at the beginning of cell growth (around 100-200 cells) and the ability to detect cell morphology to separate normal growth from elongation as described below. Objective lens 43 may comprise a 10× objective lens and/or a 5MP camera for a larger dynamic range and/or a bigger sample of each test well 20) while maintaining enough resolution to count the microbes therein. In some exemplary embodiments of optics system 9, only one picture or image per test well 20 per pass is acquired by objective lens 43. Objective lens 43 may focus slightly off the bottom of test well 20 to eliminate background noise from the bottom of test well 20. In some versions of optics system 9, objective lens 43 is configured to focus approximately 5-10 microns from the bottom of test well 20. In some versions of optics system 9, objective lens 43 is configured to focus 8 microns from the bottom of test well 20. Objective lens 43 may also include a Z-stage 44 for allowing objective lens 43 to move in the Z-axis, relative to XY-stage 37. Thus, between XY-stage 37 moving AST array holder 23 in the XY plane and Z-stage 44 moving objective lens 43 in the Z-axis, each test well 20 of array holder 23 may be moved in any three-dimensional space to precisely align test wells 20 with the frame of AST camera 35. Tube lens 45 may be embodied in an achromatic tube lens. AST camera 35 may comprise a Sony IMX253 camera or any other suitable kind of camera. In some versions of optics system 9, XY-stage 37 and Z-stage 44 are replaced with an XYZ-stage to provide all three axes of three-dimensional movement of test wells 20.

Figure 6:
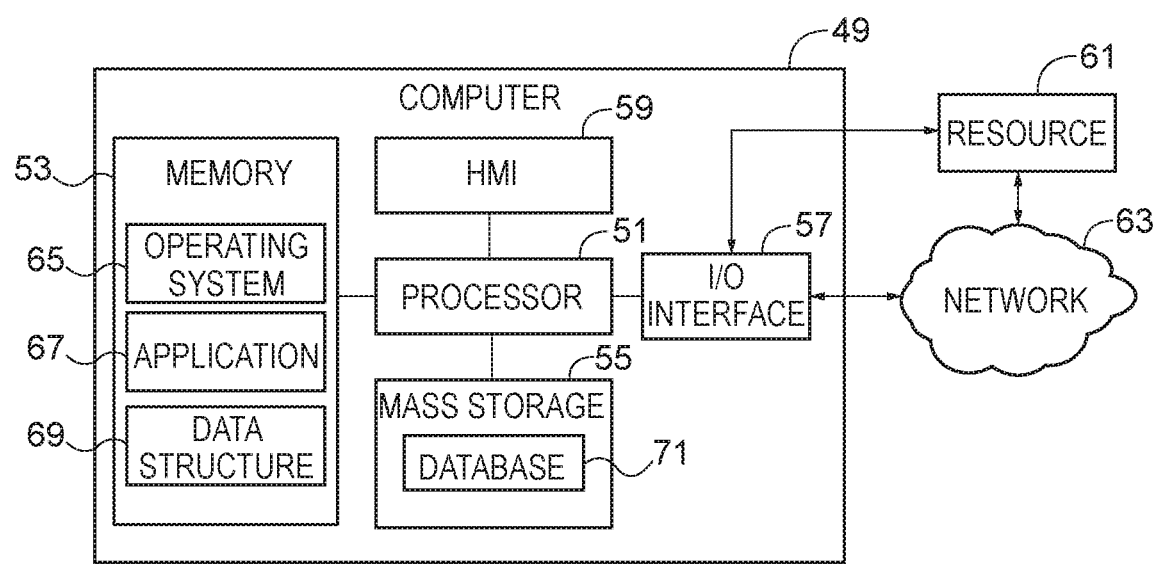
FIG. 6 depicts a diagrammatic view of an exemplary computer system.

Referring now to FIG. 6, the various components of biological testing system 1 may incorporate one or more computing devices or systems, such as exemplary computer system 49. For example, any one of consumable preparation system 3, inoculating system 5, incubator system 7, and/or optics system 9 may incorporate one or more computing systems such as exemplary computer system 49. Alternatively, each of these subsystems of biological testing system 1 may function via commands from one overall computing system such as exemplary computer system 49.

Computer system 49 may include a processor 51, a memory 53, a mass storage memory device 55, an input/output (I/O) interface 57, and a Human Machine Interface (HMI) 59. Computer system 49 may also be operatively coupled to one or more external resources 61 via a network 63 or I/O interface 57. External resources may include, but are not limited to, servers, databases, mass storage devices, peripheral devices, cloud-based network services, or any other suitable computer resource that may used by computer system 49.

Processor 51 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in memory 53. Memory 53 may include a single memory device or a plurality of memory devices including, but not limited, to read-only memory (ROM), random access memory (RAM), volatile memory, non-volatile memory, static random access memory (SRAM), dynamic random access memory (DRAM), flash memory, cache memory, or any other device capable of storing information. Mass storage memory device 55 may include data storage devices such as a hard drive, optical drive, tape drive, non-volatile solid state device, or any other device capable of storing information.

Processor 51 may operate under the control of an operating system 65 that resides in memory 53. Operating system 65 may manage computer resources so that computer program code embodied as one or more computer software applications, such as an application 67 residing in memory 53, may have instructions executed by the processor 51. In an alternative embodiment, processor 51 may execute application 67 directly, in which case the operating system 65 may be omitted. One or more data structures 69 may also reside in memory 53, and may be used by processor 51, operating system 65, or application 67 to store or manipulate data.

The I/O interface 57 may provide a machine interface that operatively couples processor 51 to other devices and systems, such as network 63 or external resource 61. Application 67 may thereby work cooperatively with network 63 or external resource 61 by communicating via I/O interface 57 to provide the various features, functions, applications, processes, or modules comprising embodiments of the invention. Application 67 may also have program code that is executed by one or more external resources 61, or otherwise rely on functions or signals provided by other system or network components external to computer system 49. Indeed, given the nearly endless hardware and software configurations possible, persons having ordinary skill in the art will understand that different versions of the invention may include applications that are located externally to computer system 49, distributed among multiple computers or other external resources 61, or provided by computing resources (hardware and software) that are provided as a service over network 63, such as a cloud computing service.

HMI 59 may be operatively coupled to processor 51 of computer system 49 in a known manner to allow a user to interact directly with the computer system 49. HMI 59 may include video or alphanumeric displays, a touch screen, a speaker, and any other suitable audio and visual indicators capable of providing data to the user. HMI 59 may also include input devices and controls such as an alphanumeric keyboard, a pointing device, keypads, pushbuttons, control knobs, microphones, etc., capable of accepting commands or input from the user and transmitting the entered input to the processor 51.

A database 71 may reside on mass storage memory device 55, and may be used to collect and organize data used by the various systems and modules described herein. Database 71 may include data and supporting data structures that store and organize the data. In particular, database 71 may be arranged with any database organization or structure including, but not limited to, a relational database, a hierarchical database, a network database, or combinations thereof. A database management system in the form of a computer software application executing as instructions on processor 51 may be used to access the information or data stored in records of the database 71 in response to a query, where a query may be dynamically determined and executed by operating system 65, other applications 67, or one or more modules.

II. OPTIMIZED AST SYSTEM AND METHOD

FIGS. 7-23 illustrate various features and steps of optimized AST method 101 (FIG. 19). In some versions, system 1 as discussed above may be used to facilitate some or all of the features provided in optimized AST method 101. Optimized AST method 101 includes performing an image analysis cycle 102 repetitively until a MIC is determined.

Figure 7:
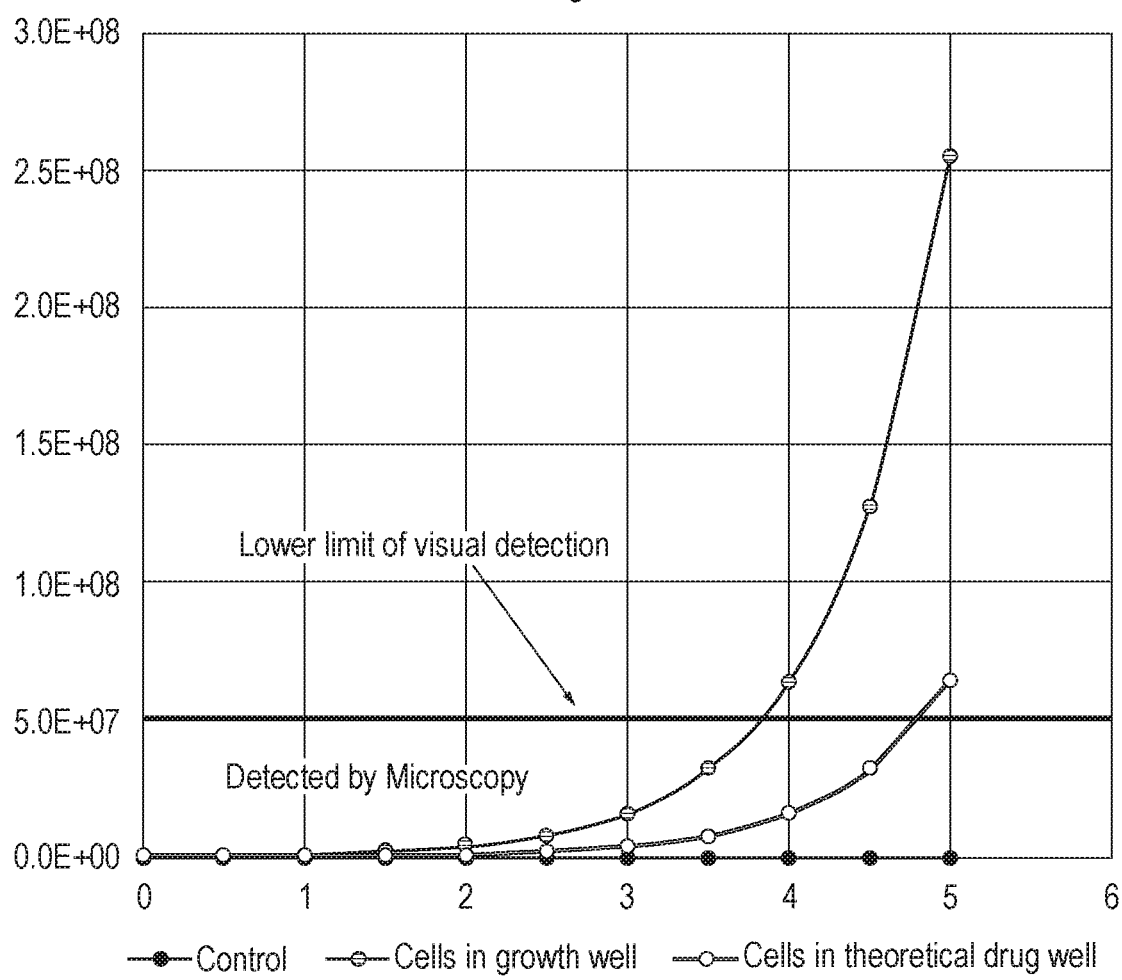
FIG. 7 depicts a chart of theoretical growth curves for a microbe.

In some conventional processes, MIC is determined through manual visual inspection of test wells after waiting a period to allow the microbes to grow. However, as shown in FIG. 7, microbial sample growth within the test wells is not observable with the naked eye until between four to ten hours after the inoculum is disposed in the test wells. Traditional methods of determining MIC are limited by what a human can visually perceive relative to the growth of the microbes within the test wells. Further, the presence of antimicrobic dilution concentrations that are below the MIC concentration may slow the growth rate, and take even longer to perceive. As shown in FIG. 7, the first six to seven doublings of the microbial sample cannot be observed visually by the human eye.

However, the information provided through these initial doublings is often indicative of the MIC. As shown in FIGS. 7-23, optimized AST method 101 utilizes digital microscopy to monitor growth rate from the point of inoculation in the test well and thus allows for more rapid and accurate detection of the MIC. In addition, specimen morphology information, such as the size and shape of the microbe, can be used to enhance the accuracy of the MIC determination. For example, specimen morphology information such as elongation may be used to enhance the accuracy of the MIC determination, as visual observation cannot detect between abnormal growth such as elongation caused by beta-lactam antibiotics and normal growth.

Figure 8:
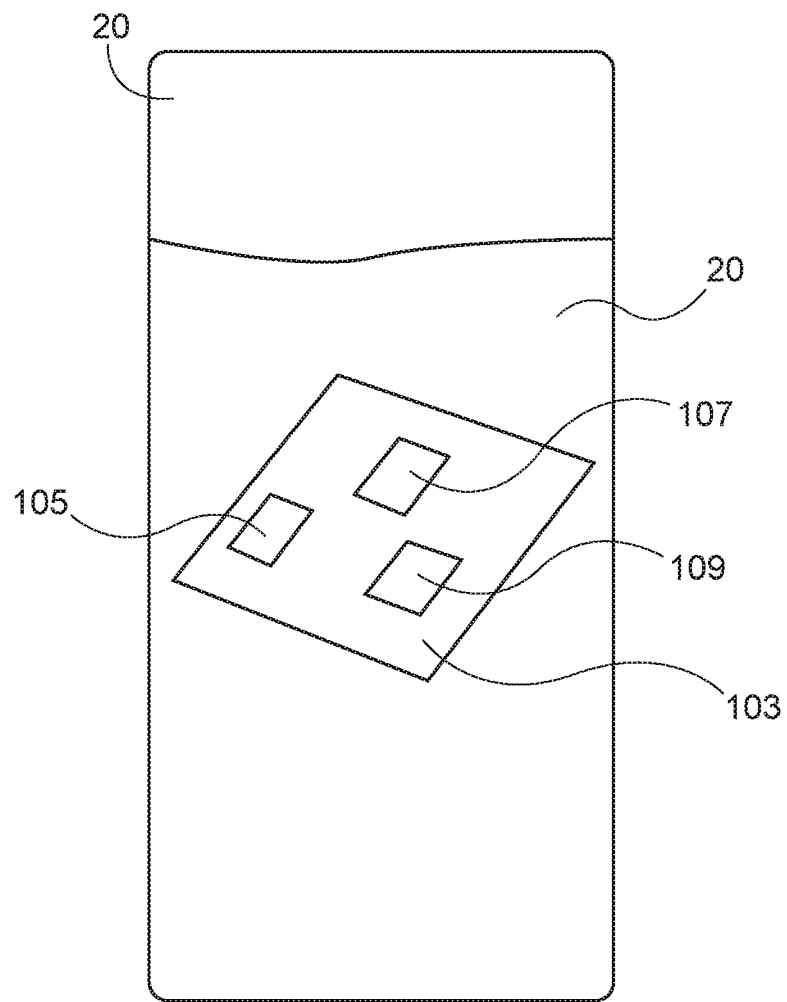
FIG. 8 depicts a schematic view of an exemplary growth test well for use in the biological testing system of FIGS. 1A and 1B.

FIG. 8 provides several exemplary digital microscopy parameters for use in optimized AST method 101. Test well 20 is embodied by a "384" style test well, having a clear viewing bottom. The volume of inoculum in test well 20 may be set to 20 microliters to reduce the amount of materials such as bulk diluents required by AST method 101 and/or minimize light artifacts and provide sampling of a consistent number of microbes from the 1:250 dilution of the 0.5 MacFarland inoculum. Decreasing the volume of inoculum in test well 20 generally increases the light artifacts. In some instances, capturing a single vertical plane 103 at 20× objective whereby AST camera 35 is set at 0.33 microns/pixel may be sufficient for sampling the inoculum and ensuring that each individual microbe is recognizable. However, these parameters are configurable and may change as desired by the user or the underlying needs of the system. Capturing three focal sites spaced about 5 microns apart within single vertical plane 103 may also provide a sufficient number of microbes in the sample to count for use in optimized AST method 101. These three focal sites are labeled site 105, site 107, and site 109 in FIG. 8. In an exemplary version of optimized AST method 101, each focal site is approximately 700×700 microns within single vertical plane 103, rather than capturing three sites in three different vertical planes. AST camera 35, optics system 9, and computer 49 are configured to capture an image of each focal site in consecutive time periods, manipulate each of these images, and thereafter use the data derived from these manipulated images to make a MIC determination.

Figure 9:
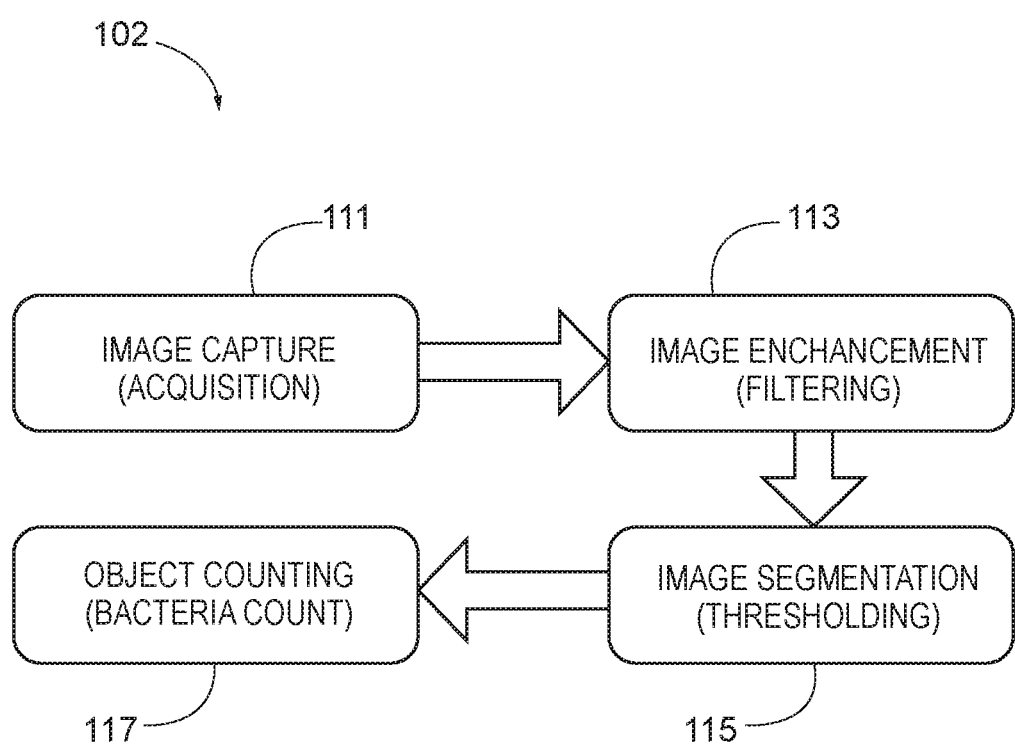
FIG. 9 depicts an exemplary image analysis cycle for use in the biological testing system of FIGS. 1A and 1B.

Image analysis cycle 102 is generally depicted in FIG. 9 and comprises an image capture step 111, an image enhancement step 113, an image segmentation step 115, and an object counting step 117. Optimized AST method 101 includes performing image analysis cycle 102 repetitively until a MIC is determined. Image analysis cycle 102 utilizes one or more instances of computer 49 and the various elements thereof to perform image capture step 111, image enhancement step 113, image segmentation step 115, and object counting step 117, as well as any sub steps provided therein.

Figure 10:
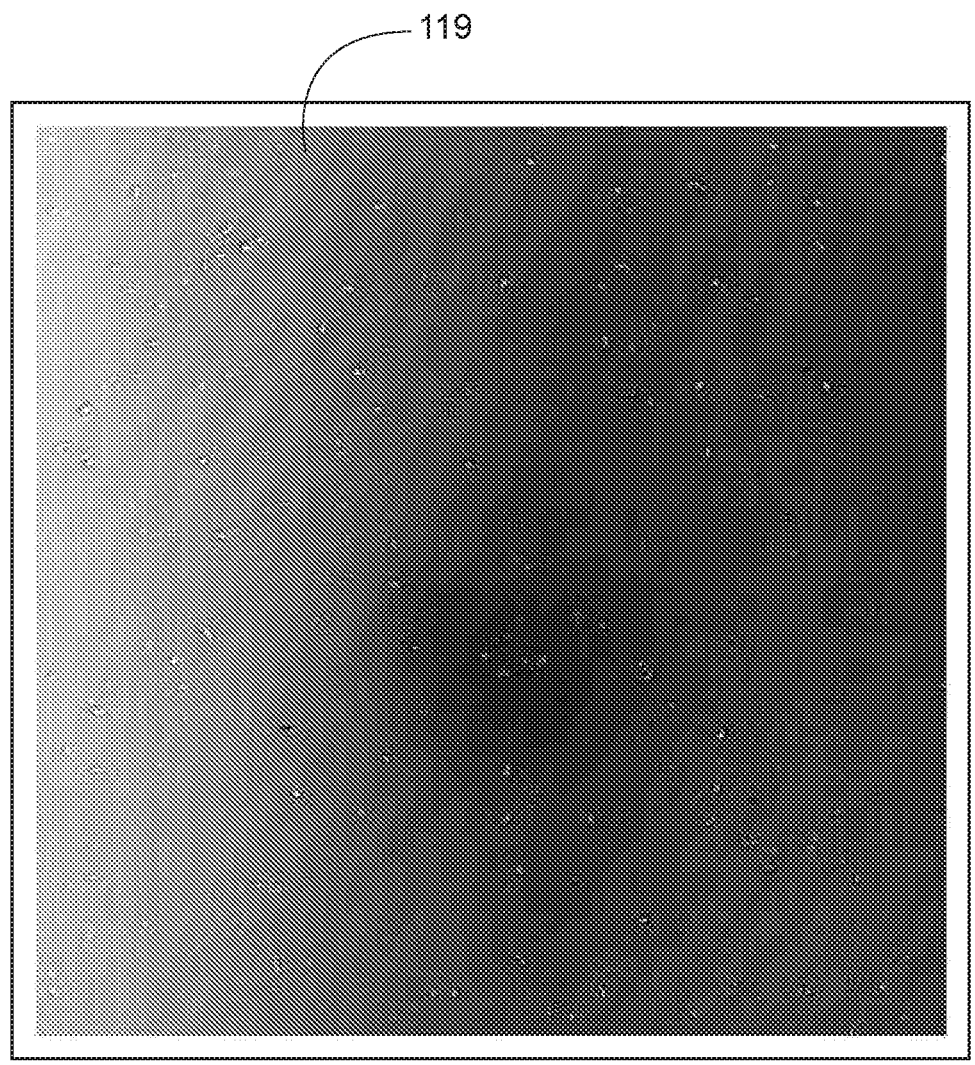
FIG. 10 depicts an exemplary raw image captured by the optics system of FIG. 2.
Figure 11:
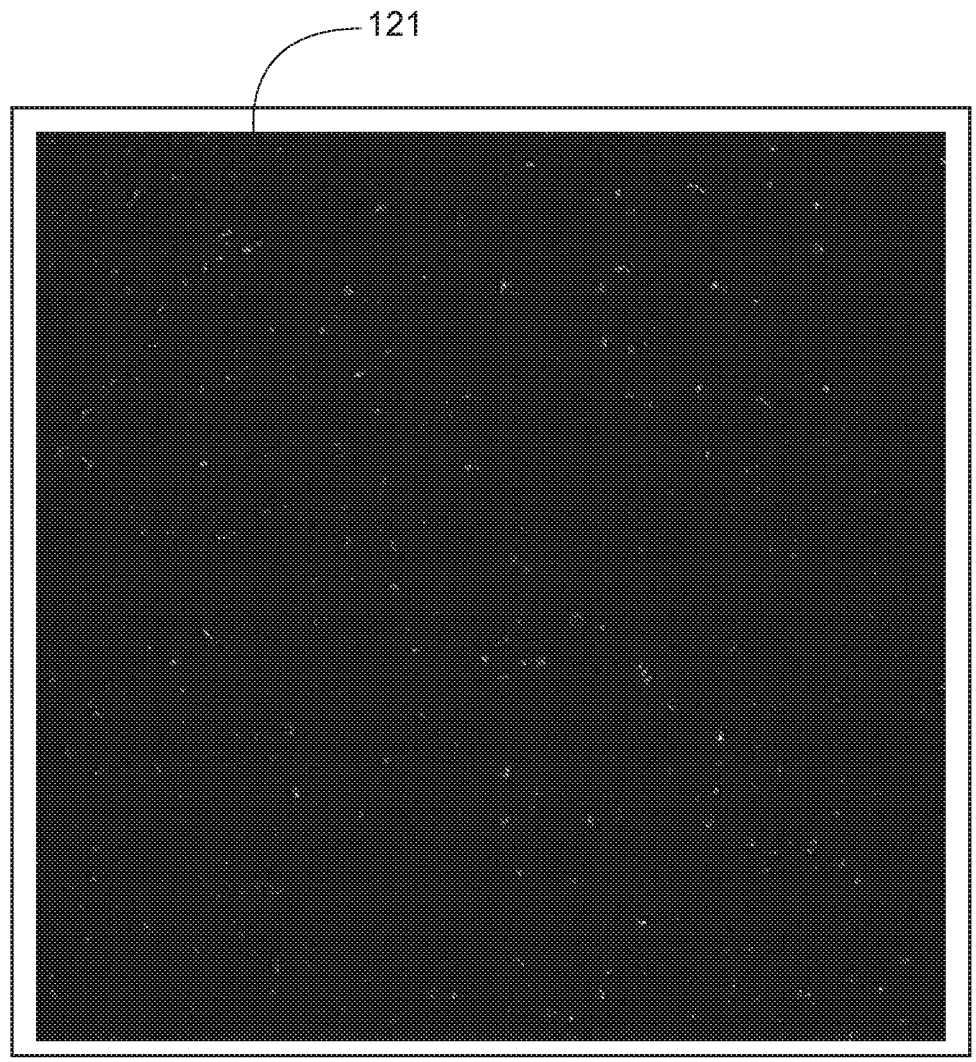
FIG. 11 depicts an exemplary enhanced image derived from the raw image of FIG. 10.

Image analysis cycle 102 begins with image capture step 111 captures a raw image 119 (FIG. 10) of the inoculum via AST camera 35 of optics system 9 and stores raw image 119 in memory 53. While raw image 119 is depicted as a single image, raw image 119 may be a composite of several separate images taken in vertical plane 103, for example, a composite of site 105, site 107, and site 109. Raw image 119 may also be a composite of several images taken in different planes within the inoculum sample or may be a single image. As illustrated in FIG. 10, raw image 119 may include deficiencies such as uneven illumination. Uneven illumination may be a result of the meniscus created by the inoculum in combination with the walls of the associated test well 20, which may affect the path of illumination source 41. Uneven background intensity may also be caused by environmental issues such as plastic deformation or from a variety of other sources. After raw image 119 is captured in image capture step 111, image capture step 111 moves to image enhancement step 113.

Figure 12:
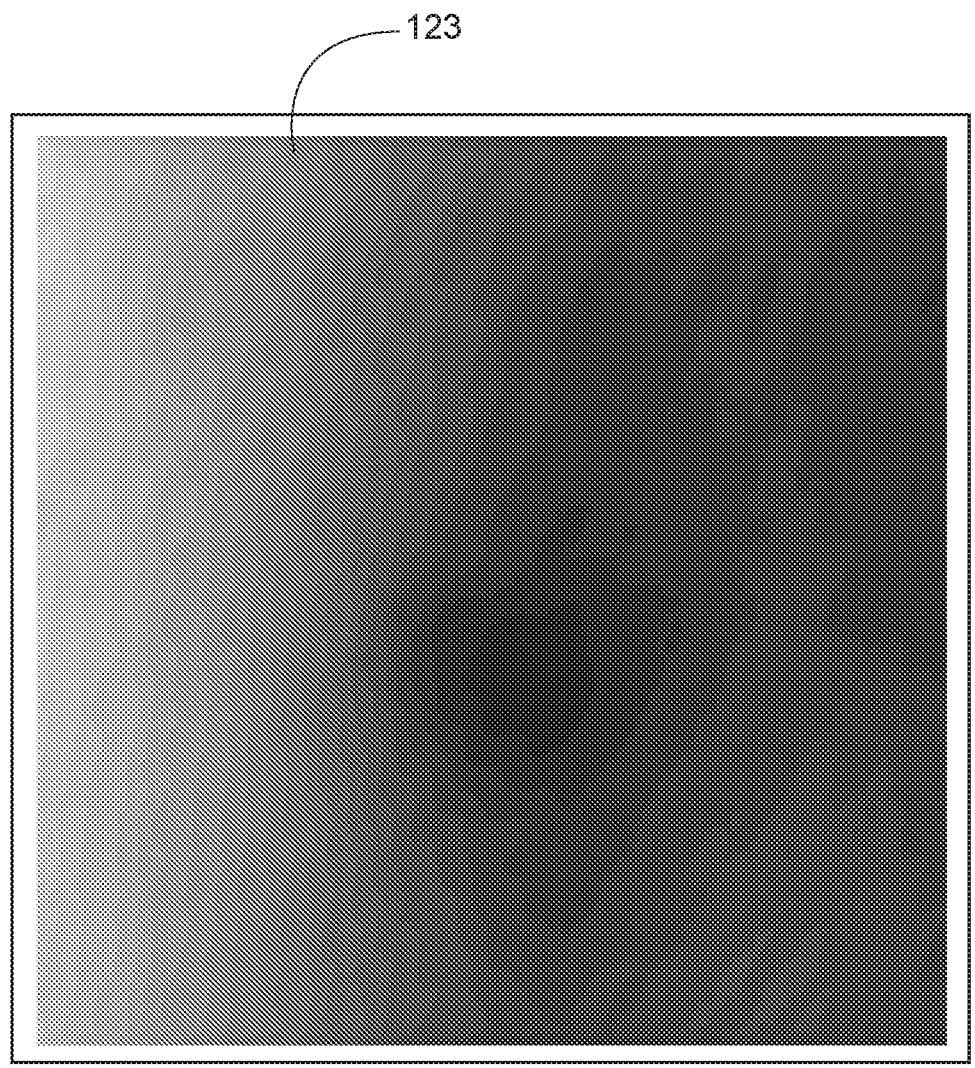
FIG. 12 depicts an exemplary gradient image derived from the raw image of FIG. 10.

As shown in FIGS. 9, and 11-14, image enhancement step 113 processes raw image 119 to create an enhanced image 121 (FIG. 11), whereby enhanced image 121 is more suitable for the process of counting and recognizing microbes such as bacteria. During image enhancement step 113, one or more attributes of raw image 119 are modified. These attributes may include basic gray level transformations, noise filtering, and median filtering. For example, to resolve the problem of non-uniform illumination, a median filter may be applied to raw image 119 to arrive at a gradient image 123 (FIG. 12). This may be accomplished by selecting a pixel radius sufficient to provide a resulting image containing only the gradient of the background illumination of raw image 119. Gradient image 123 is then subtracted from raw image 119 to correct for the uneven illumination and generate enhanced image 121 free of uneven illumination.

Figure 13:
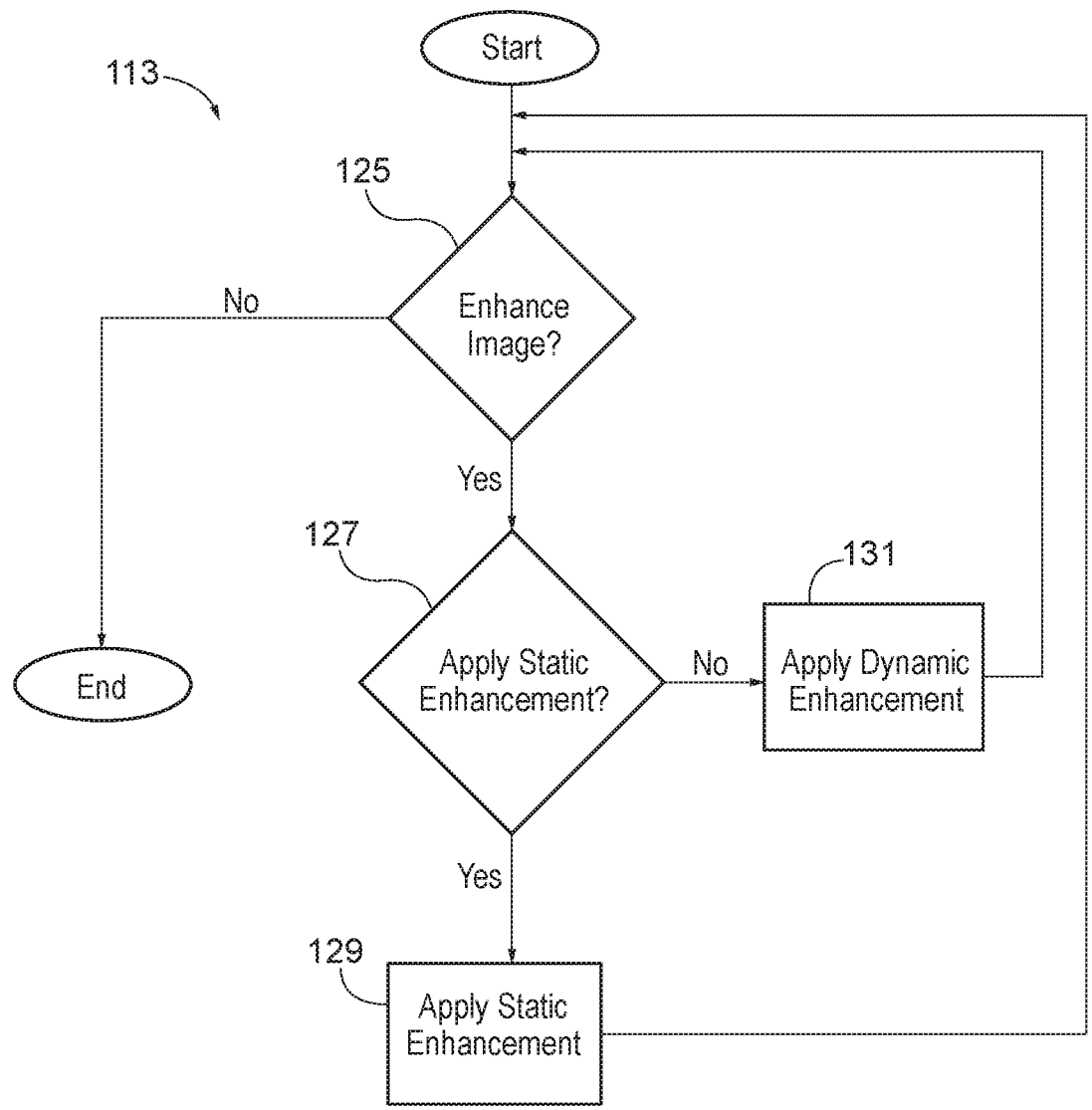
FIG. 13 depicts an exemplary image enhancement flowchart.

Image enhancement step 113 may apply image enhancements either statically, dynamically, or both. For example, the pixel radius for the median filter may be a statically set constant value, or may be adaptively derived dynamically from characteristics of each raw image 119 captured through optics system 9. As shown in FIG. 13, some versions of image enhancement step 113 may include a step 125, whereby a determination is made as to whether the working image should undergo enhancement. If step 125 determines the working image should be enhanced, step 125 proceeds to a step 127. In step 127, a determination is made as to whether a static enhancement should be applied. If step 127 determines a static enhancement should be applied, step 127 proceeds to a step 129. If step 127 determines a static enhancement should not be applied, step 127 proceeds to a step 131. In step 127, a static enhancement is applied to the working image and step 127 proceeds back to step 125. In step 131, a dynamic enhancement is applied to the working image and step 131 proceeds back to step 125. If step 125 determines the working image should not be further enhanced, step 125 proceeds to end.

Figure 14:
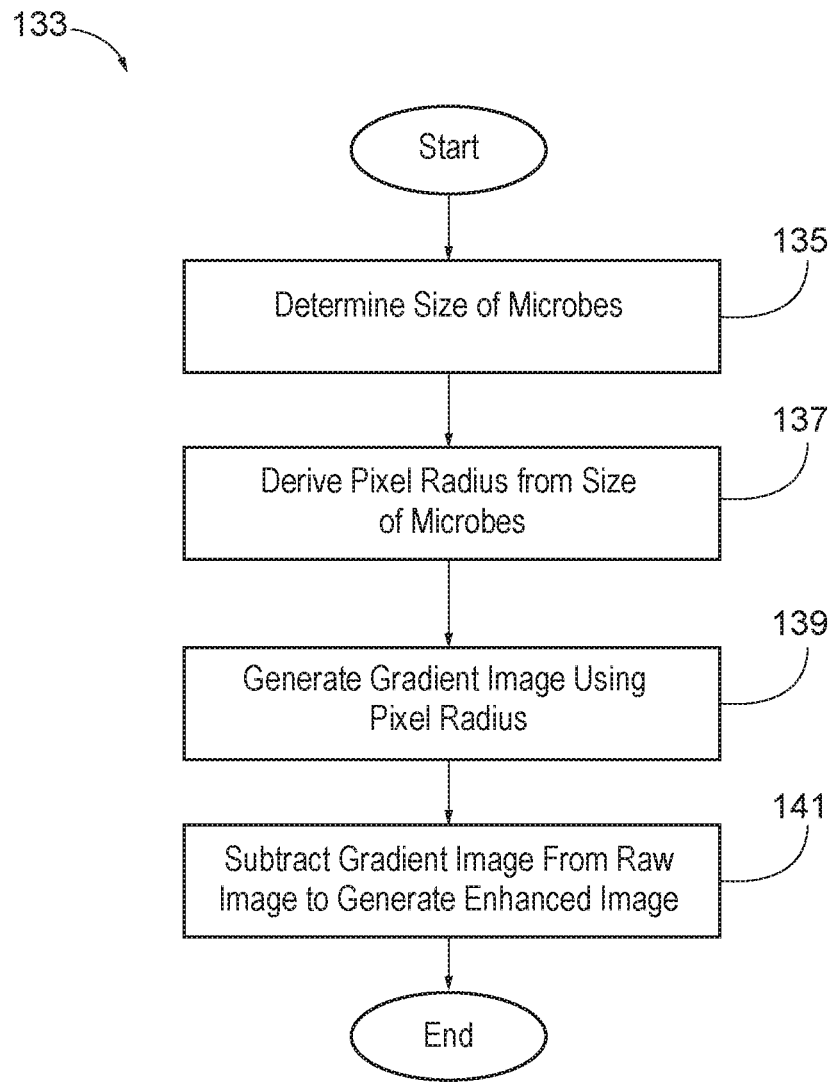
FIG. 14 depicts an exemplary dynamic image enhancement flowchart.

FIG. 14 illustrates an example of a method of dynamic image enhancement 133. Method of dynamic image enhancement 133 is directed to dynamically determining the appropriate pixel radius for use in a median filter enhancement. Method of dynamic image enhancement 133 begins with a step 135, whereby the size of the microbes depicted in raw image 119 is determined. Microbes may be in the form of gram-positive bacteria, gram-negative bacteria, yeast, or any other biological element or microorganism. The size of the microbes in raw image 119 may change depending on various circumstances and parameters associated with the inoculum and the overall optics system 9. Thus, while the literal size of the particular microbe being tested is generally constant in nature, the relative size of the microbes depicted in raw image 119 is dynamic and variable because of differences in parameters such as the lens objectification. Once step 135 determines the size of the microbes in raw image 119, step 135 proceeds to a step 137. In step 137, the pixel radius is derived from the determined size of the microbes. As a general example, if step 135 determines the maximum length of any given microbe in raw image 119 is five pixels, the pixel radius may be determined to be greater than five so that the filtered image only represents the gradient contained in the background. After step 135 derives the pixel radius based off the dynamically determined size of the microbes, step 135 proceeds to step 139. In step 139, gradient image 123 is generated based on processing raw image 119 with the derived pixel radius. After gradient image 123 is generated, step 139 moves to a step 141. In step 141, gradient image 123 is subtracted from raw image 119 to generate enhanced image 121. Thereafter, method of dynamic image enhancement 133 proceeds to end.

Figure 15:
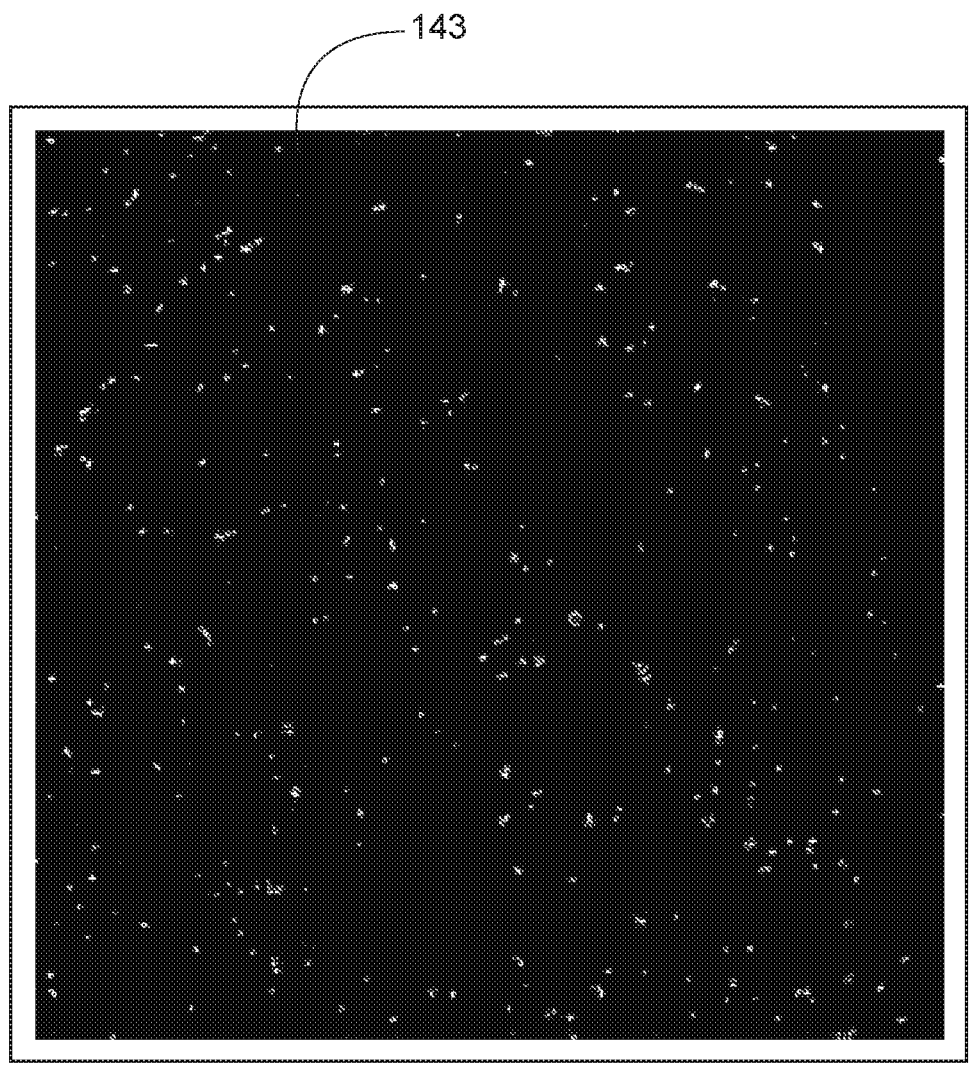
FIG. 15 depicts an exemplary segmented image derived from the raw image of FIG. 10.
Figure 16:
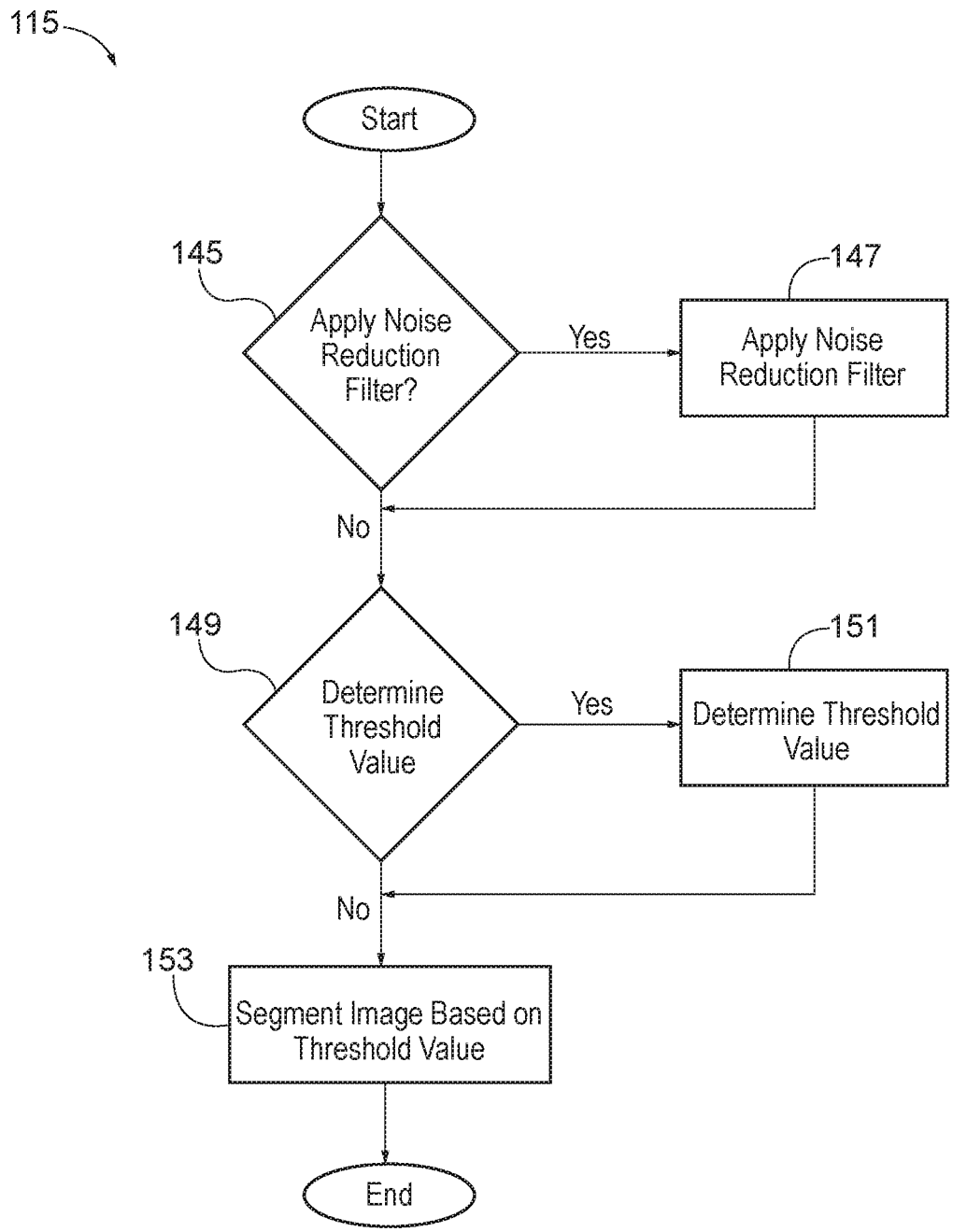
FIG. 16 depicts an exemplary image segmentation flowchart.

As shown in FIGS. 9, 15, and 16, image segmentation step 115 is used to partition the image into distinct regions containing pixels representing either the microbes as the foreground or the background. Image segmentation step 115 converts enhanced image 121 into a segmented image 143, as shown in FIG. 15. Image segmentation step 115 produces a binary image from enhanced image 121, where every pixel is equal to a value of either 0 or 1, where 0 refers to the background and 1 refers to a portion of a particular microbe.

Image artifacts such as noise may be removed by applying a noise reduction filter prior to applying the segmentation algorithm. Segmentation can be obtained using static threshold value or using an adaptive image thresholding method such as the Otsu cluster based thresholding algorithm. In this algorithm, the gray-level samples are clustered in two parts as background and foreground (object), or alternatively are modeled as a mixture of two Gaussians. The threshold value for the particular image thresholding algorithm used may be determined dynamically, depending on the overall image provided to image segmentation step 115 and the relative grayscale levels of the image. For example, inoculating system 5 or another element of system 1 may be configured to apply nigrosin to each test well 20 to enhance the image, as nigro sin does not attach to certain microbes such as bacteria. This may alter the relative greyscale levels in raw image 119 and require a different threshold value for the segmentation algorithm, as compared to a raw image 119 without nigrosin. In some versions of optimized AST method 101, threshold values may be determined dynamically by searching for edges within several areas of the image. These edges are the transition point between the background and a microbe. Thus, the threshold value can then be calculated as the average greyscale value for pixels on each side of the located edge.

As shown in FIG. 16, some versions of image segmentation step 115 may begin with a step 145. In step 145, a determination is made regarding whether to apply a noise reduction filter to enhanced image 121. If step 145 determines a noise reduction filter should be applied, step 145 proceeds to a step 147 where the noise reduction filter is applied. Step 147 thereafter proceeds to a step 149. If step 145 determines that a noise reduction filter should not be applied, step 145 proceeds directly to step 149. In step 149, a decision is made regarding whether to dynamically determine a threshold value. If step 149 decides a threshold value should be dynamically determined, step 149 proceeds to a step 151 where the threshold value is determined. Step 149 thereafter proceeds to a step 153. If step 149 decides not to dynamically determine a threshold value, a static predetermined threshold value is used and step 149 proceeds directly to step 153. In step 153, enhanced image 121 is segmented using the selected threshold value and step 153 and thereafter image segmentation step 115 proceeds to end.

Once image segmentation step 115 generates segmented image 143, image segmentation step 115 proceeds to object counting step 117. In object counting step 117, the background and foreground pixels are considered to derive information regarding the number of microbes in the sample, the area occupied by the microbes in the sample, and the ratio between the number of microbes and the area occupied by the microbes. In some versions of object counting step 117, the actual microbe count is compared with an average microbe count to determine if an error occurred within the image capture process. The comparison may incorporate a standard deviation with the average microbe count to generalize the microbe comparison.

Object counting step 117 may be configured to derive information regarding the number of microbes in the image. In some embodiments of object counting step 117, the number of foreground pixels in segmented image 143 may be counted in accordance with a predefined width and/or length to determine the number of microbes in the imaged portion of the inoculum. The counting algorithm may be divided into two separate algorithms, one for counting rod shaped microbes and one for counting spherical shaped microbes as the profile of the underlying microbes provides a corresponding different foreground pixel shape in segmented image 143. For example, the counting algorithm may be configured to consider a square of 2×2 pixels a microbe for counting purposes for spherical shaped microbes, or may consider a rectangle of 1×4 pixels a microbe for counting purposes for rod shaped microbes. Further, the counting algorithm may be configured to process both algorithms in order to capture the different three-dimensional orientations of rod shaped microbes. For example, if an elongated rod is positioned endwise towards AST camera 35, it will have a much different profile when viewed in two dimensions through AST camera 35. Therefore, both of the counting algorithms may be used during the counting phase of image analysis cycle 102. Alternatively, the counting algorithm may be configured to consider and count any foreground pixels surrounded by background pixels as a microbe.

Object counting step 117 may be configured to derive information regarding the total area occupied by all of the microbes in the image. In some versions of object counting step 117, the total number of foreground pixels in segmented image 143 may be counted and compared to the total number of background pixels in segmented image 143. Object counting step 117 may express the area count information in any format, including as a percent such as 30%, or as a literal number of pixels such as "138 foreground pixels out of 450 total pixels" or "138 foreground pixels and 312 background pixels."

Object counting step 117 may be configured to derive information regarding the ratio between the total area occupied by all of the microbes in the image and the total count of microbes. This information may be useful by determining whether the microbes are undergoing elongation over time. Elongation is a precursor to death and indicates the concentration of the antimicrobic dilution is negatively affecting the microbes. More specifically, elongation may occur when microbes such as bacteria encounter an effective amount of antibiotic drugs.

Figure 17:
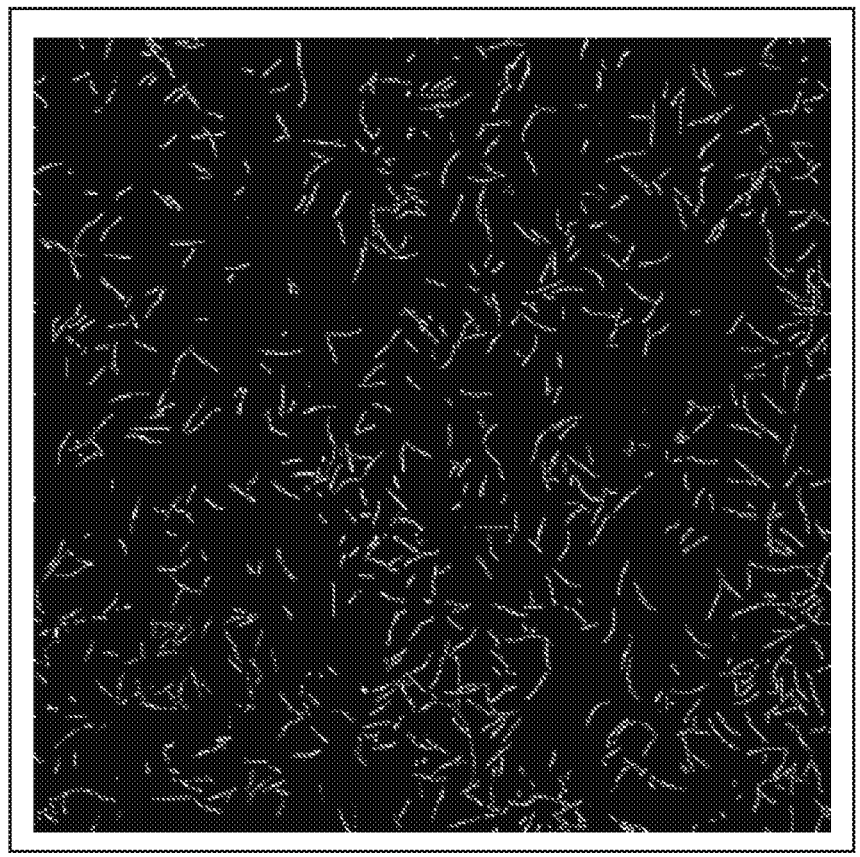
FIG. 17 depicts exemplary microbes having elongated elements.
Figure 18:
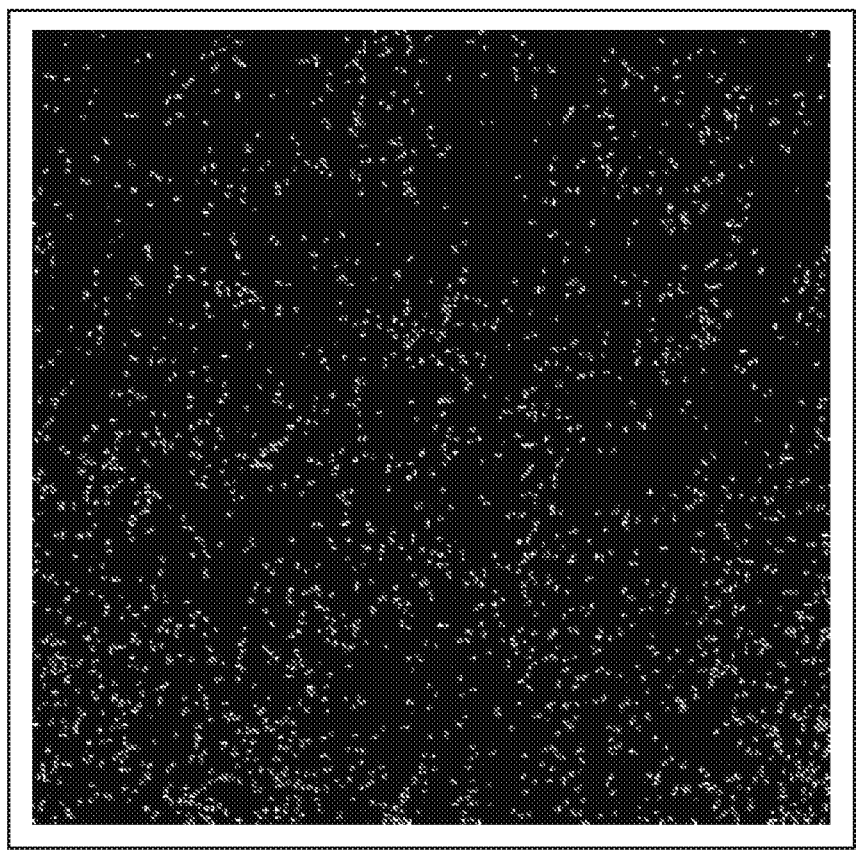
FIG. 18 depicts exemplary microbes having non-elongated elements.

For example, FIGS. 17 and 18 depict microbes embodied by *E. coli* bacteria. FIG. 17 depicts the *E. coli* after being exposed to a dilution of the antibiotic ampicillin, while FIG. 18 depicts the *E. coli* free from any ampicillin exposure. FIG. 17 illustrates abnormal growth in the form of elongation as a result of the ampicillin exposure. This elongation is a precursor to the death of the bacteria and illustrates that the concentration of ampicillin is sufficient to neutralize the bacteria. FIG. 18 illustrates normal growth. It follows that the ratio between the total area occupied by all of the bacteria and the bacteria count will increase over time to represent each bacterium elongating. For example, if a particular image sample includes 100 bacteria and each bacterium measures approximately 4 pixels each, the area occupied by the 100 bacteria within the image is 400 pixels. In this image sample, the ratio of bacteria area to bacteria count is 4.0. Over time, if each bacterium in the sample elongates to approximately 12 pixels each, the area occupied by the 100 bacteria in a later image is 1200 pixel and the ratio of bacteria area to bacteria count in this later image is 12.0. This increase in ratio indicates that the concentration of ampicillin is effective in neutralizing the *E. coli* bacteria because the bacteria are elongating, which in turn indicates an impending death.

Once object counting step 117 derives the desired information from segmented image 143, image analysis cycle 102 terminates. Optimized AST method 101 iteratively performs image analysis cycle 102 at set time intervals to determine how the microbes in each test well 20 are changing and reacting to the particular antimicrobic dilution pairing. Further, optimized AST method 101 iteratively performs image analysis cycle 102 on each test well 20 associated with the microbes to determine how the microbes are reacting to each concentration of the antimicrobic dilution. For example, presume the microbes being tested are *E. coli* bacteria and three test wells 20 are being tested, with each test well 20 having a 20-microliter solution therein. The first test well 20 may contain a antimicrobic dilution of 1 microgram per milliliter (mcg/ml), the second test well 20 may contain a antimicrobic dilution of 2 mcg/ml, and the third test well 20 may contain a antimicrobic dilution of 4 mcg/ml. Optimized AST method 101 performs image analysis cycle 102 on each of the three test wells at each set time interval to determine (a) how each antimicrobic dilution is affecting the microbes; and (b) how each antimicrobic dilution is performing relative to the other antimicrobic dilutions. If the data indicates the 1 mcg/ml antimicrobic dilution is as effective as the 2 and 4 mcg/ml antimicrobic dilutions at neutralizing the microbes, the 1 mcg/ml antimicrobic dilution is the MIC.

An exemplary version of optimized AST method 101 is illustrated in FIG. 19 and begins with a step 155. In step 155, the system waits for a set time period threshold to allow the microbes within the selected test well 20 enough time to provide new information regarding the growth rate or reaction to the particular antimicrobic dilution. Optimized AST method 101 may be configured to utilize any given static or dynamic time period threshold. For example, some bacteria or yeast or other microbes may react very quickly and provide information relevant to making an MIC determination within an hour. In this scenario, optimized AST method 101 may be configured to perform image analysis cycle 102 every five minutes to capture data regarding the rapidly changing environment within test wells 20. Other microbes may react relatively slowly to antimicrobic dilutions, and therefore a time period threshold of one hour may be more appropriate. Once step 155 waits the specified time period threshold, step 155 moves to a step 157.

In step 157, one iteration of image analysis cycle 102 is performed on a particular microbe with a selected test well 20. As discussed above, an iteration of image analysis cycle 102 derives data regarding the growth rate of the microbes within the selected test well 20. After an iteration of image analysis cycle 102 is performed, step 157 moves to a step 159. In step 159, the data collected in step 157 is stored and/or updated in memory, which may be in the form of a database, a flat file, or any other similar memory or storage device. In some embodiments of optimized AST method 101, step 159 stores the data collected in step 157 in database 71 (FIG. 6). Once step 159 stores/updates the collected data, step 159 moves to a step 161.

In step 161, optimized AST method 101 determines whether enough data has been collected to determine a MIC. If more data is needed to accurately determine a MIC, step 161 returns to step 155 and waits to perform another image analysis cycle 102 to collect more data at a future time interval. If step 161 determines a sufficient amount of data has been collected, step 161 proceeds to a step 163. Step 161 considers not only the data collected with respect to the particular test well 20 associated with the microbes and the antimicrobic dilution, step 161 considers all of the data collected for all of the test wells 20, as the relative growth rates of the microbes vis a vis the other test wells 20 and antimicrobic dilutions is indicative of the MIC.

Figure 20A:
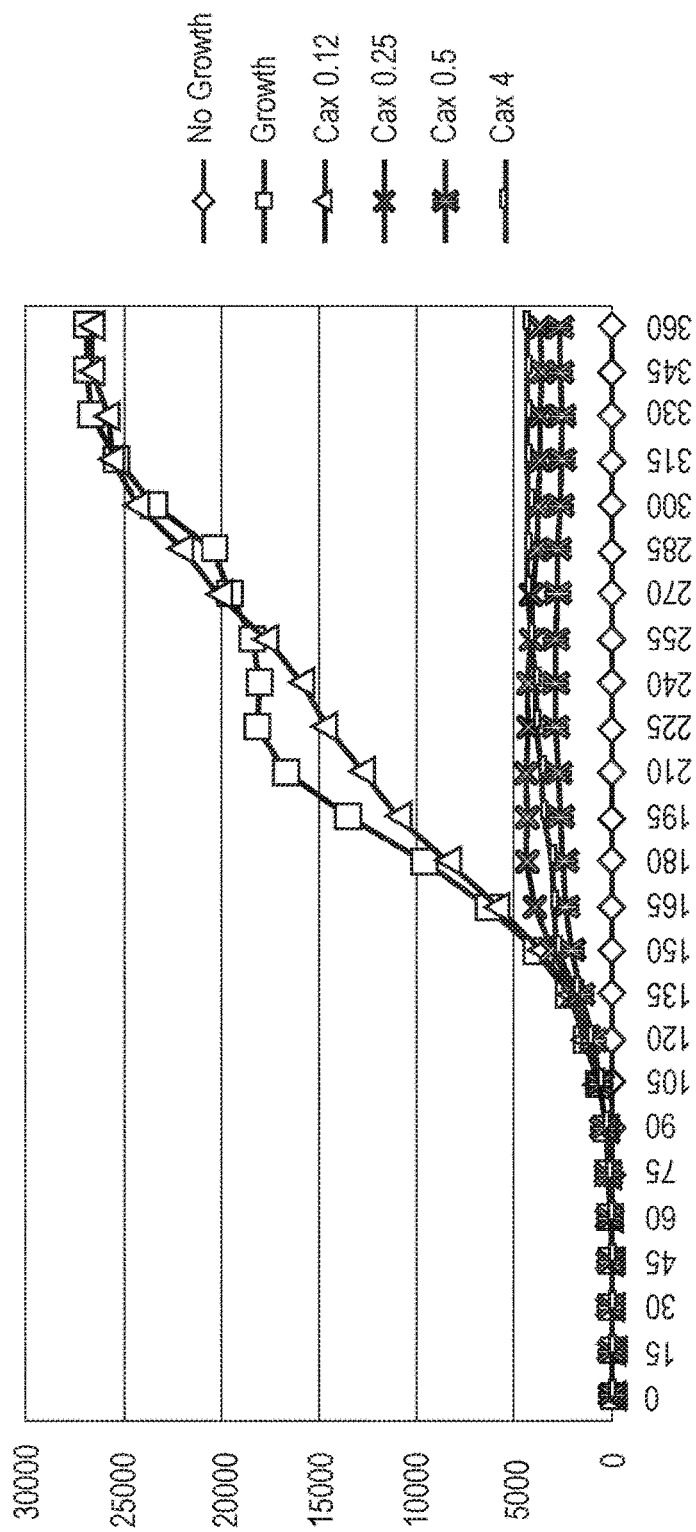
FIG. 20A depicts an exemplary chart of successive microbe counts for a plurality of different antimicrobic dilutions.
Figure 20B:
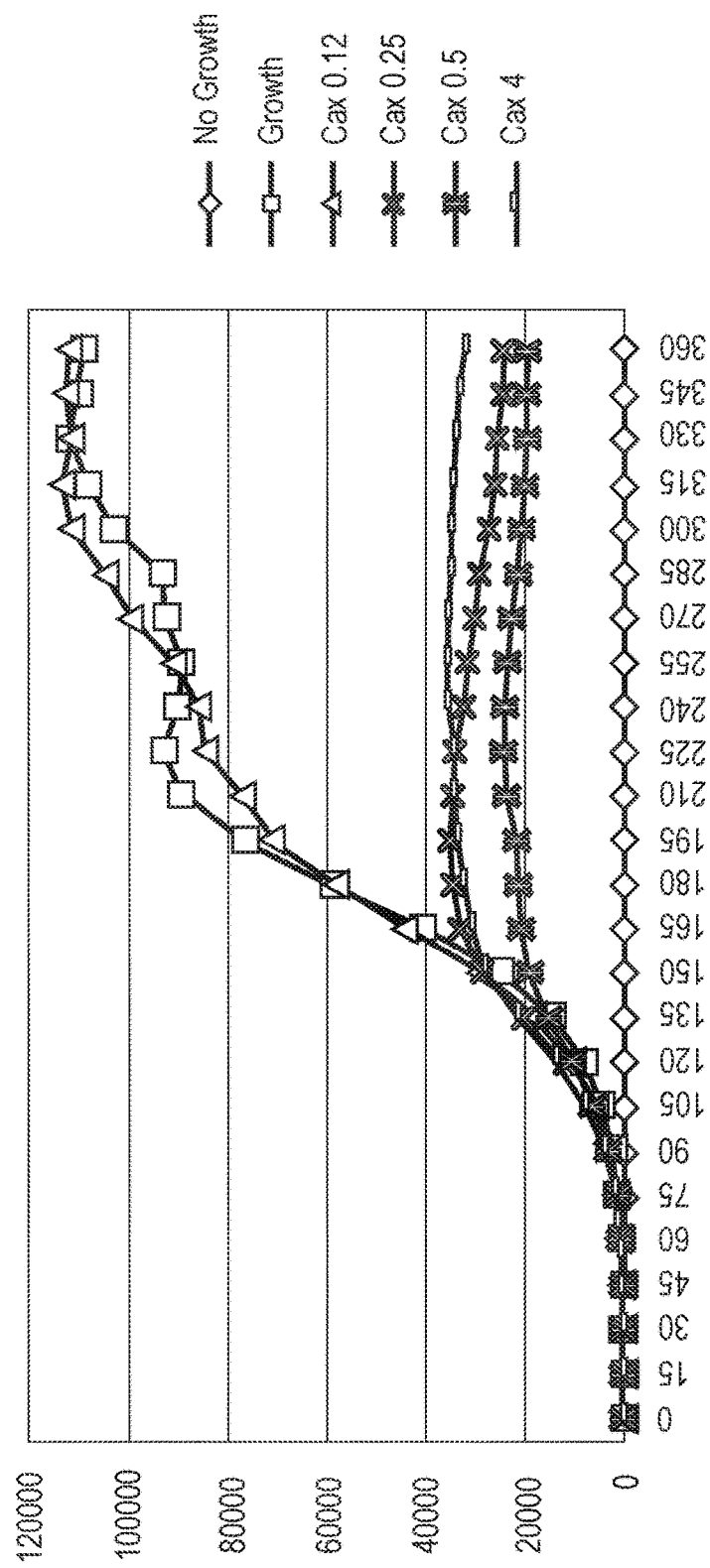
FIG. 20B depicts an exemplary chart of successive area summations for the antimicrobic dilutions of FIG. 20A.
Figure 20C:
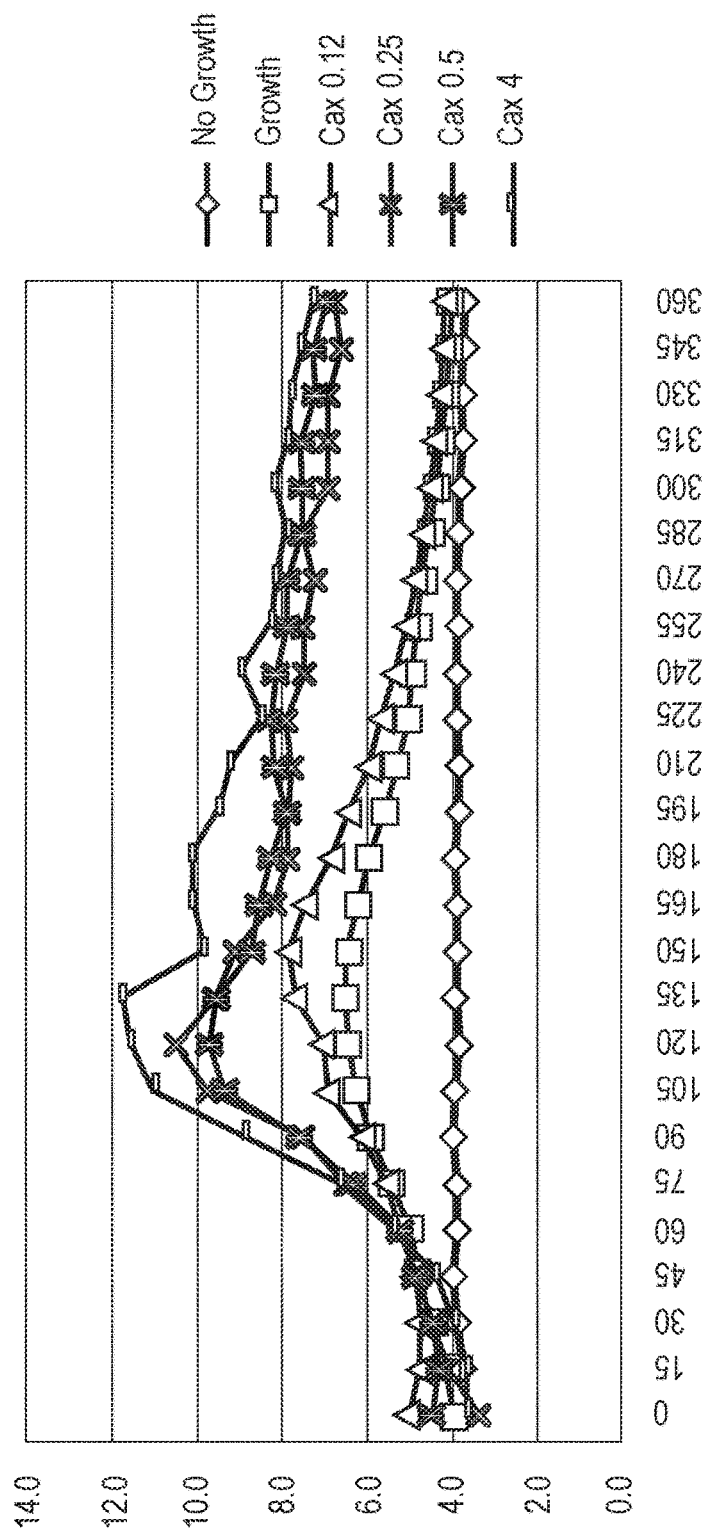
FIG. 20C depicts an exemplary chart of successive determinations of the ratio between the area summations of FIG. 20B and the microbe counts of FIG. 20A.

In step 163, the MIC is determined. The determination is based on the data collected during each iteration of image analysis cycle 102 for all of the antimicrobic dilutions for a microbial sample. As shown in FIGS. 20A, 20B, and 20C, the determination may be based on the counts of each bacterium or other microbe in each image (FIG. 20A), the area occupied by the microbes in each image (FIG. 20B), or the ratio data regarding the occupied area relative to the count of the microbes in each image (FIG. 20C).

FIG. 20A depicts "count sum" information, whereby the sum of the bacteria count in each concentration of antibiotic is plotted to show relative bacteria count over time. As shown in FIG. 20A, the "Cax 0.12" dilution appears to have no effect on the *E. coli* sample, as the bacteria count increases generally along the same curve as the Growth sample, which includes a growth broth but is free from any antimicrobic such as an antibiotic. The minimum amount of antimicrobic dilution to have an effect on the *E. coli* sample is the "Cax 0.25" dilution and therefore, it can be determined that the Cax antibiotic applied at 0.25 dilution is the MIC.

FIG. 20B depicts "area sum" information, whereby the area of the bacteria in each concentration of antibiotic is plotted to show relative aggregate size of the bacteria population over time. The "area sum" information provided in FIG. 20B may be used to confirm the determination of FIG. 20A, as "Cax 0.25" is the minimum amount of antibiotic to have the desired effect on the area occupied by the *E. coli* bacteria. FIG. 20B conveys that the bacteria are not increasing in count (as shown by the comparison between the "Growth" and the "Cax 0.12" chart lines), but is increasing in area. Thus, the bacteria are elongating and experiencing abnormal growth as a result of the bacteria's impending death due to the antibiotic in the antimicrobic dilution.

FIG. 20C depicts "area/count ratio" information, whereby the ratio between the "count sum" and the "area sum" data is plotted to show relative differences in bacteria populations vis a vis area for each concentration of antibiotic. The elongation data is more pronounced in FIG. 20C, where the ratio between the area and count is depicted. As seen in the "No Growth" chart line where the bacteria are not supplied with a growth broth, the ratio of area to count is flat, at approximately 4.0. This indicates each bacterium is around 4 pixels in size and the bacteria are neither increasing in count nor experiencing elongation. The chart lines reflecting the "Growth" and the "Cax 0.12" increase in ratio, but the gradual increase indicates that both the count of the bacteria and the area is increasing. The large spikes in ratio to above 8.0 indicate elongation of the bacteria, as the area increases but the overall count of the bacteria remains constant. The least amount of antibiotic experiencing this pronounced elongation spike is the "Cax 0.25" sample and therefore the ratio data of FIG. 20C also provides an MIC 0.25 in confirmation of the same MIC determination provided by the data in FIGS. 20A and 20B.

Figure 21:
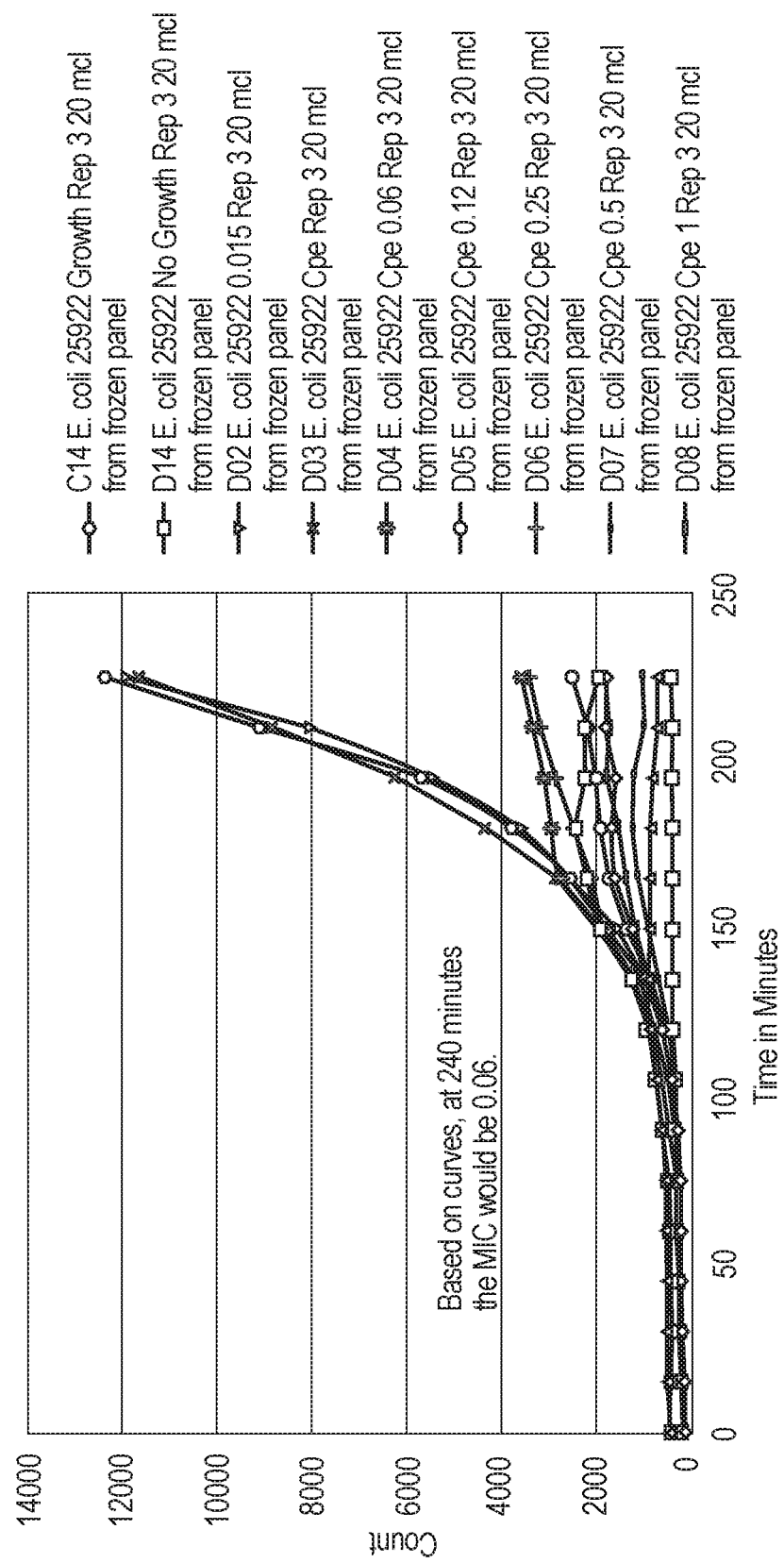
FIG. 21 depicts an exemplary chart of successive microbe counts for a plurality of different antimicrobic dilutions.
Figure 22:
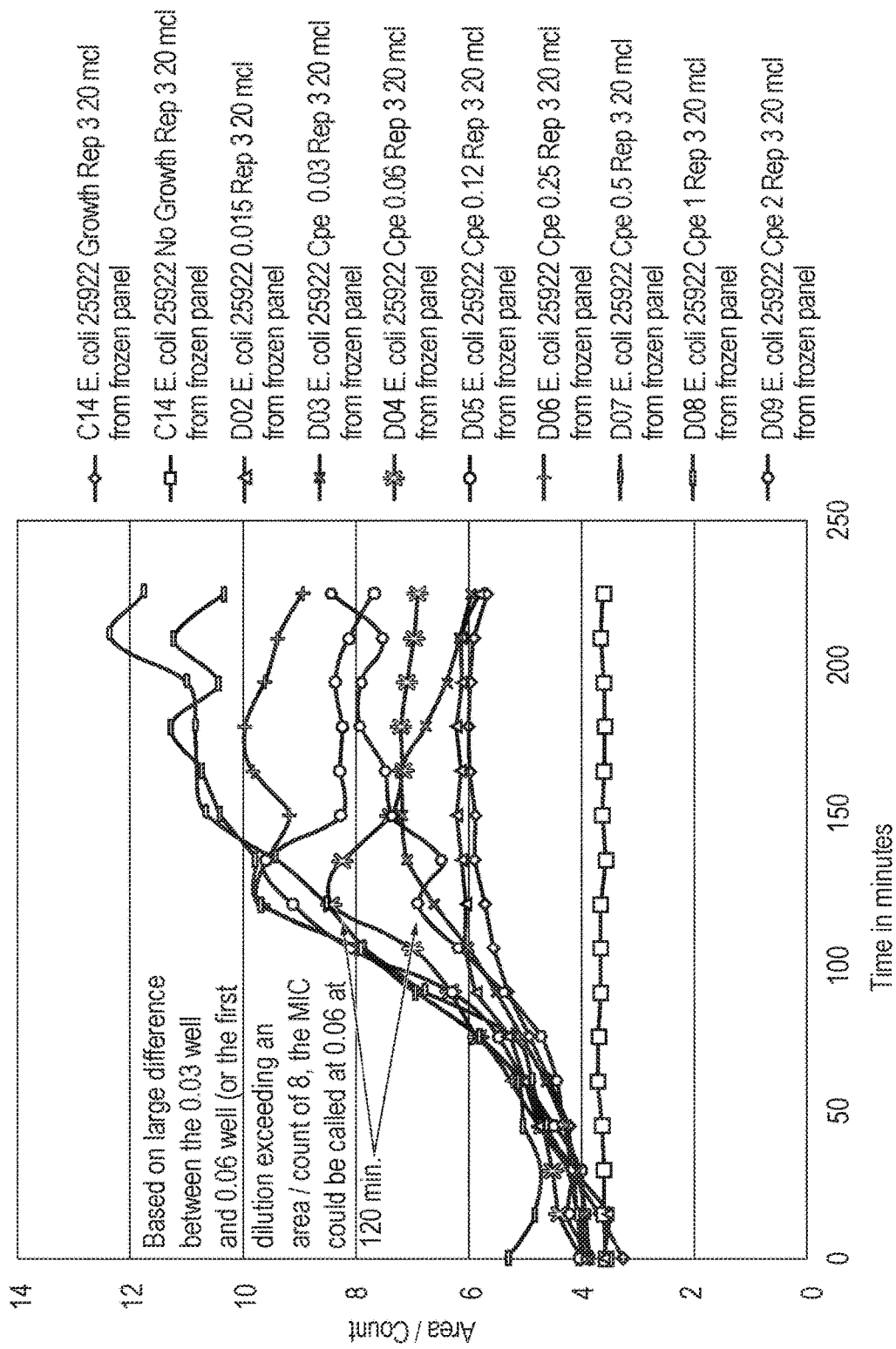
FIG. 22 depicts an exemplary chart of successive determinations of the ratio between area summations for the microbes of FIG. 21 and the microbe counts of FIG. 21.

The MIC determination may also be based on various combinations of the data collection formats and the general trend of the data over time, or one set of data may be used to determine the MIC, while another set may be used to confirm the determined MIC. Any combination of the above described "count sum," "area sum," and "area/count ratio" mechanism may be used to determine or confirm the MIC. For example, FIGS. 21 and 22 illustrate data points collected every fifteen minutes for an *E. coli* sample tested with various antimicrobic dilutions of the antibiotic Cefepime. At around the 200-minute mark, the bacteria count data provided in FIG. 21 indicates the "Cpe 0.06" dilution is the MIC. The ratio data provided in FIG. 22 indicates "Cpe 0.06" is the MIC at around the 120-minute mark, as all of the antimicrobic dilutions above "Cpe 0.03" provide an elongation spike at around the 120-minute mark. Therefore, a preliminary determination of MIC may be made using the ratio data (FIG. 22) at 120 minutes, and the confirmation of the determined MIC may be made using the count data (FIG. 21) at 200 minutes. This embodiment of optimized AST method 101 therefore provides a two-fold testing of the data, with a preliminary MIC determination available at 120 minutes and a confirming MIC determination available at 200 minutes. With reference to FIG. 9, four hours or 240 minutes is the earliest possible threshold for making a MIC determination using the manual visual inspection method, which is less accurate and more labor intensive.

III. DIGITAL MICROSCOPY ALGORITHMS FOR DETERMINING MINIMUM INHIBITORY Concentration (MIC)

Figure 23:
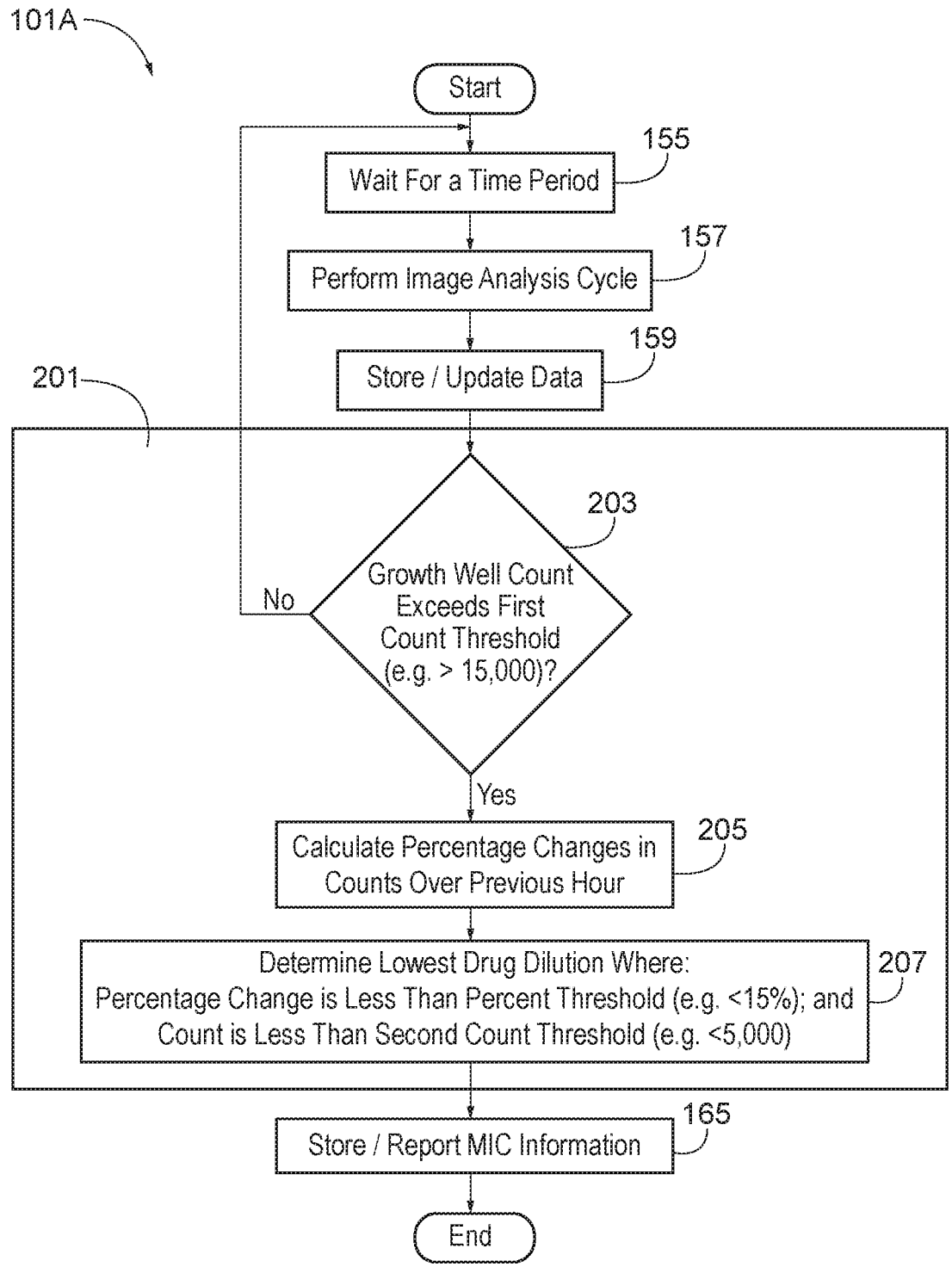
FIG. 23 depicts an exemplary optimized antimicrobial susceptibility testing method of the present invention, similarly to FIG. 19.

FIG. 23 depicts another version of exemplary optimized AST method 101, referred to hereinafter as method 101A with like elements having like features. Method 101A incorporates an exemplary digital microscopy algorithm for determining MIC, depicted in FIG. 23 as method 201. Method 201 may be executed in place of steps 161 and 163 of method 101.

As shown in FIG. 23, after image data is updated and stored, step 159 proceeds to method 201. Method 201 begins with a step 203, whereby a determination is made regarding the count of the microbes in the growth well. As shown in FIGS. 20A, 20B, and 20C, each AST test array 23 may include a test well 20 where inoculum 18 is disposed therein free from any antimicrobial agents such as an antibiotic. The growth well therefore illustrates the uninhibited growth of the particular microbes undergoing testing. Step 203 determines whether the count of the microbes in the growth well has exceed a first count threshold. In some versions of method 201, the first count threshold may be a set static count amount. For example, the first count threshold may be 15,000 microbes. In other versions of method 201, the first threshold amount may be configured by the user of biological testing system 1 each time a new test or batch of tests are initiated. In yet some other versions of method 201, the first count threshold may be dynamically set for each test based upon the results of the ID test performed on the microbes by biological testing system 1 and ID fluorimeter.

If step 203 determines the number of microbes in the growth well has not exceeded the first count threshold, step 203 returns to step 155 to perform another iteration of the time period wait step (step 155), image analysis cycle step (step 157), and storing/updating data step (step 159). If step 203 determines the number of microbes in the growth well has exceeded the first count threshold, step 203 proceeds to a step 205.

In step 205, the percentage changes of the microbe count for each test well 20 in AST array holder 23 are calculated over the past immediate period of time. In some versions of step 205, the period of time may be the previous hour or the time period reflected in step 155. For example, if the microbe count in test well 20A (not shown) increases from 1000 microbes to 1200 microbes over the previous hour, the percentage change calculated in step 205 is 20%. In this manner, each test well 20 in AST array holder 23 is calculated and thereafter step 205 proceeds to a step 207.

Step 207 determines the MIC by utilizing the percentage changes calculated in step 205 as well as the current microbe count for each test well. Specifically, step 207 determines which test wells 20 include both a percentage change less than a percent threshold and a microbe count less than a second count threshold. The lowest antimicrobial drug dilution meeting these two qualifications is determined to be the MIC. As noted above with respect to the first count threshold, the percentage threshold and/or the second count threshold may be static parameters, or inputted by the user at the initiation of testing, or may be dynamically changed to reflect the results of the ID testing performed by the ID fluorimeter 33 for the particular microbe. For example, in some versions of step 207, the percent threshold may be 15% and the second count threshold may be 5,000 microbes. In this example, if the data depicted in Table 1 below is collected by biological testing system 1, the MIC will be the 0.5 dilution found in test well 20c because this is the lowest antimicrobial drug dilution that satisfies both criteria. Namely, the antimicrobial drug dilution of test well 20c is the lowest tested dilution that includes both a percentage change less than 15% and a microbe count of less than 5,000. Test well 20b includes a microbe count of less than 5,000 but the percentage change is 17%. Similarly, the percentage change of test well 20a is 12% but the microbe count is 6,500. Test well 20d satisfies both criteria but the antimicrobial dilution is greater than test well 20c.

TABLE 1

| Test Well | Dilution of Antimicrobic | Microbe Count: Hour 1 | Microbe Count: Hour 2 | Percent Change |
|---|---|---|---|---|
| Growth | N/A | 12,000 | 15,600 | 30% |
| 20a | 0.12 | 5,800 | 6,500 | 12% |
| 20b | 0.25 | 4,100 | 4,800 | 17% |

TABLE 1-continued

| Test Well | Dilution of Antimicrobic | Microbe Count: Hour 1 | Microbe Count: Hour 2 | Percent Change |
|---|---|---|---|---|
| 20c | 0.5 | 3,800 | 4,100 | 7% |
| 20d | 1.0 | 3,400 | 3,700 | 8% |

Once step 207 determines the lowest antimicrobial dilution that satisfies both criteria, step 207 supplies the MIC to step 165 and method 101A proceeds accordingly to store and report the MIC information.

Figure 24:
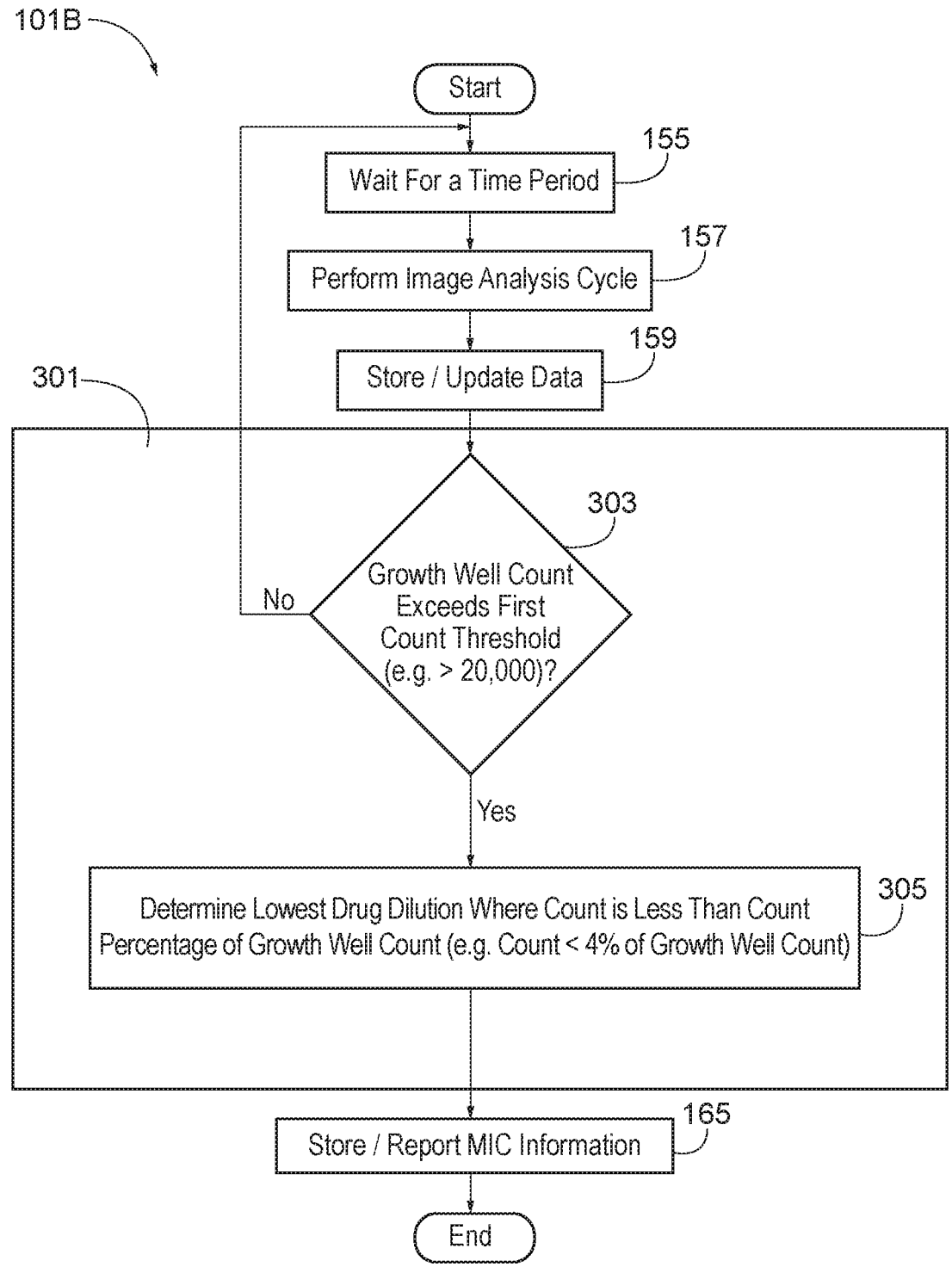
FIG. 24 depicts an exemplary optimized antimicrobic susceptibility testing method of the present invention, similarly to FIG. 19.

FIG. 24 depicts another version of exemplary optimized AST method 101, referred to hereinafter as method 101B with like elements having like features. Similar to method 101A, method 101B incorporates an exemplary digital microscopy algorithm for determining MIC, depicted in FIG. 24 as method 301. Method 301 may be executed in place of steps 161 and 163 of method 101. Method 301 may be useful with slow to express resistance mechanisms in microbes such as those with carbapenem resistance, especially due to a metallo-beta lactamase. Some microbes with slow to express resistance do not visually appear to start growth until four hours or more. However, the sensitivity AST camera 35 allows for assessing small increases in growth from the moment an antimicrobial agent present is introduced.

Method 301 begins with a step 303, whereby a determination is made regarding whether the microbe count of the growth well is greater than a first count threshold. As described with first count threshold of method 201, first count threshold may be a static parameter, a user inputted parameter, or may be dynamically changed based on the results of the ID test for the microbe. For example, the first count threshold may be 20,000. In this example, step 303 would return to step 155 upon a determination that the growth well count is less than 20,000. If the growth well count is greater than 20,000, step 303 proceeds to a step 305.

Step 305 determines the MIC by comparing the microbe count of each test well to the microbe count of the growth well. The MIC is determined to be the lowest antimicrobial drug dilution associated with a microbe count that is less than a count percentage of the microbe count of the growth well. As described with first count threshold of method 201, the count percentage parameter may be a static parameter, a user inputted parameter, or may be dynamically changed based on the results of the ID test for the microbe. For example, the count percentage may be 4% of the growth well count and method 101B may include the data depicted in Table 2 below. In this scenario, test well 20c is the MIC because it is the lowest antimicrobial drug dilution associated with a microbe count that is less than 4% of the growth well count. Test well 20d also satisfies the criterion but has a higher dilution than test well 20c.

TABLE 2

| Test Well | Dilution of Antimicrobic | Current Microbe Count | Percent of Growth Well Count |
|---|---|---|---|
| Growth | N/A | 22,000 | N/A |
| 20a | 0.12 | 5,800 | 26% |
| 20b | 0.25 | 4,100 | 18% |
| 20c | 0.5 | 440 | 2% |
| 20d | 1.0 | 220 | 1% |

Once step 305 determines the lowest antimicrobial drug dilution that satisfies criterion, step 305 supplies the MIC to step 165 and method 101B proceeds accordingly to store and report the MIC information.

Some versions of method 201 and/or method 301 may incorporate previously discussed concepts such as "area-sum" information (FIG. 20B) and "area/count ratio" information (FIG. 20C) to aid in determining the MIC for a given antimicrobial agent.

IV. MAPPING RESULTS

Some versions of method 201 and/or method 301 may incorporate a mapping of the results to allow for recommending an antimicrobial therapy without providing a specific MIC for a given antimicrobial agent. In some versions of method 201 and/or method 301, the dilution range of the antimicrobial agent is truncated. For example, an MIC of 16 or 32 could be mapped to a result of ">=8" or (greater than or equal to 8). This information would allow the antimicrobial therapy to proceed without providing a specific MIC.

V. DETERMINING MICROBE RESISTANCE SYSTEM AND METHOD

The growth pattern information derived from optics system 9 may also be combined with a fluorogenic test measuring a change in pH to detect some mechanisms of resistance in the microbes being tested. As an example, one of the fluorogenic test substrates could be an antimicrobial agent. Degradation of the antimicrobial agent leads to a change in the pH of the medium within two hours after inoculation, and the pH change can be detected with an indicator that changes fluoresces with changes in pH. Combining the information on the growth patterns (cell count, area, and area/count), as described above, along with an indication that the antimicrobial agent has degraded provides a way to quickly ascertain if the microbe is resistant and helps to determine the MIC of the organism.

For example, the antibiotic Meropenem is enzymatically degraded by microbes such as gram negative bacteria carrying the *Klebsiella pneumonia* carbapenemase (KPC) resistance mechanism. If Meropenem is degraded, the medium drops in pH. The fluorogenic pH indicator, MEU (methyl-lumbeliferone) will change (decrease) in fluorescence with that change. This change occurs within 1 to 2 hours. If the particular microbe is identified within 2 hours through ID testing, the pH changes for a test well containing Meropenem within 1-2 hours, and the growth pattern is identified through the area count methods described above, we can predict that the MIC will be greater than 1 mcg/ml, and that the micro-organism is resistant to several antibiotics.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method comprising: (a) capturing a raw image of a mixture, wherein the mixture includes a plurality of microbes and an antimicrobial agent; (b) enhancing the raw image into an enhanced image; and (c) determining a microbe count associated with the enhanced image, wherein the microbe count is based on the number of microbes in the plurality of microbes depicted in the enhanced image.

Example 2

The method of Example 1 or any of the subsequent Examples, further comprising: (a) prior to enhancing the raw image, determining a size of the microbes in the plurality of microbes depicted in the raw image; and (b) enhancing the raw image into the enhanced image based at least in part on the size.

Example 3

The method of any of the previous or subsequent Examples, further comprising: (a) determining a threshold value for the enhanced image; and (b) segmenting the enhanced image based at least in part on the threshold value.

Example 4

The method of any of the previous or subsequent Examples, further comprising: (a) deriving a pixel radius from the size; (b) generating a gradient image of the raw image based at least in part on the pixel radius; and (c) enhancing the raw image into the enhanced image based at least in part on the gradient image.

Example 5

A method comprising: (a) capturing a raw image of a mixture, wherein the mixture includes a plurality of microbes and an antimicrobial agent; (b) enhancing the raw image into an enhanced image; (c) segmenting the enhanced image into a segmented image; and (d) counting an amount of microbes depicted in the segmented image.

Example 6

The method of any of the previous or subsequent Examples, further comprising applying a noise reduction filter to the enhanced image prior to the segmentation of the enhanced image.

Example 7

The method of any of the previous or subsequent Examples, further comprising: (a) determining a threshold value for the enhanced image; and (b) segmenting the enhanced image based at least in part on the threshold value.

Example 8

The method of any of the previous or subsequent Examples, further comprising: (a) prior to enhancing the raw image, determining a size of the microbes in the plurality of microbes depicted in the raw image; and (b) enhancing the raw image into the enhanced image based at least in part on the size.

Example 9

The method of any of the previous or subsequent Examples, further comprising: (a) deriving a pixel radius from the size; (b) generating a gradient image of the raw image based at least in part on the pixel radius; and (c) enhancing the raw image into the enhanced image based at least in part on the gradient image.

Example 10

The method of any of the previous or subsequent Examples, further comprising: (a) adding the antimicrobial agent to the plurality of microbes in a test concentration; and (b) determining whether the test concentration is a minimum inhibitory concentration of the antimicrobial agent relative to the plurality of microbes based at least in part on the counted amount of microbes.

Example 11

A method comprising: (a) depositing a mixture into each test well in a test array, wherein the mixture in each test well includes a plurality of microbes and a differing concentration of an antimicrobial agent; (b) capturing an image of the mixture in each test well; (c) collecting a characteristic of the plurality of microbes depicted in each image; and (d) determining a minimum inhibitory concentration of the antimicrobial agent with respect to the plurality of microbes, wherein the minimum inhibitory concentration is based at least in part on the characteristic, wherein the minimum inhibitory concentration is based at least in part on the concentration of the antimicrobial agent associated with each test well.

Example 12

The method of any of the previous or subsequent Examples, further comprising enhancing the image prior to collecting the characteristic of the plurality of microbes depicted in each image.

Example 13

The method of any of the previous or subsequent Examples, further comprising: (a) prior to enhancing the image, determining a size of the microbes in the plurality of microbes depicted in the image; and (b) enhancing the image based at least in part on the size of the microbes.

Example 14

The method of any of the previous or subsequent Examples, further comprising: (a) deriving a pixel radius from the size of the microbes; (b) generating a gradient image of the image based at least in part on the pixel radius; and (c) enhancing the image into an enhanced image based at least in part on the gradient image.

Example 15

The method of any of the previous or subsequent Examples, further comprising segmenting the enhanced image prior to collecting the characteristic of the plurality of microbes depicted in each image.

Example 16

The method of any of the previous or subsequent Examples, further comprising applying a noise reduction filter to the enhanced image prior to the segmentation of the enhanced image.

Example 17

The method of any of the previous or subsequent Examples, further comprising: (a) determining a threshold value for the enhanced image; and (b) segmenting the enhanced image based at least in part on the threshold value.

Example 18

The method of any of the previous or subsequent Examples, wherein the characteristic is an amount of microbes in the plurality of microbes depicted in each image.

Example 19

The method of any of the previous or subsequent Examples, wherein the characteristic is a size of the microbes in the plurality of microbes depicted in each image.

Example 20

The method of any of the previous or subsequent Examples, wherein the characteristic is a ratio, wherein the ratio is based at least in part on an amount of microbes depicted in each image, wherein the ratio is based at least in part on the size of the microbes in the plurality of microbes depicted in each image.

Example 21

The method of any of the previous or subsequent Examples, wherein the characteristic is a ratio, wherein the ratio is based at least in part on an amount of pixels associated with the microbes in the plurality of microbes depicted in each image.

Example 22

A method comprising: (a) depositing a mixture into each test well in a test array, wherein the mixture in each test well includes a plurality of microbes and a differing concentration of an antimicrobial agent; (b) capturing a raw image of the mixture in each test well; (c) manipulating the raw image into a final image; (d) counting an amount of microbes in each final image; (e) storing the amount of microbes counted in each final image in a dataset, wherein the amount of microbes counted in each final image is associated with the concentration of the antimicrobial agent for in the test well in the dataset; (f) waiting for a time period; (g) after the time period, repeating (b), (c), (d), and (e); and (h) determining a minimum inhibitory concentration of the antimicrobial agent with respect to the plurality of microbes based on the dataset.

Example 23

The method of any of the previous or subsequent Examples, further comprising enhancing the raw image into an enhanced image, wherein the final image is based at least in part on the enhanced image.

Example 24

The method of any of the previous or subsequent Examples, further comprising: (a) determining a size of the microbes in the plurality of microbes depicted in the raw image; and (b) enhancing the raw image into the enhanced image based at least in part on the size of the microbes.

Example 25

The method of any of the previous or subsequent Examples, further comprising: (a) deriving a pixel radius from the size of the microbes; (b) generating a gradient image of the raw image based at least in part on the pixel radius; and (c) enhancing the raw image into the enhanced image based at least in part on the gradient image.

Example 26

The method of any of the previous or subsequent Examples, further comprising segmenting the enhanced image into the final image.

Example 27

The method of any of the previous or subsequent Examples, further comprising applying a noise reduction filter to the enhanced image prior to the segmenting the enhanced image into the final image.

Example 28

The method of any of the previous or subsequent Examples, further comprising: (a) determining a threshold value for the enhanced image; and (b) segmenting the enhanced image into the final image based at least in part on the threshold value.

Example 29

A biological testing system comprising: (a) an incubator system, wherein the incubator system is configured to incubate a mixture disposed in a test well for a time period, wherein the mixture includes a plurality of microbes and an antimicrobial agent; (b) an optics system comprising: (i) a stage, wherein the stage is configured to selectively receive the test well after incubating in the incubator system for the time period; and (ii) a camera, wherein the camera is configured to capture a raw image of the mixture disposed in the test well on the stage; (c) a movement system configured to move the test well between the incubator system and the optics system; (d) a database, wherein the raw image is stored in the database; and (e) a processor, wherein the processor is configured to: (i) manipulate the raw image into a final image; (ii) collect a characteristic of the mixture from the final image; and (iii) determine a minimum inhibitory concentration of the antimicrobial agent with respect to the plurality of microbes based on the characteristic.

Example 30

The method of any of the previous or subsequent Examples, wherein the stage is movable in a first direction and a second direction.

Example 31

The method of any of the previous or subsequent Examples, wherein the stage is movable in a third direction.

Example 32

The method of any of the previous or subsequent Examples, wherein the characteristic is an amount of microbes in the plurality of microbes depicted in the final image.

Example 33

The method of any of the previous or subsequent Examples, wherein the characteristic is a size of the microbes in the plurality of microbes depicted in the final image.

Example 34

The method of any of the previous or subsequent Examples, wherein the characteristic is a ratio, wherein the ratio is based at least in part on an amount of microbes depicted in the final image, wherein the ratio is based at least in part on the size of the microbes in the plurality of microbes depicted in the final image.

Example 35

The method of any of the previous or subsequent Examples, wherein the characteristic is a ratio, wherein the ratio is based at least in part on an amount of pixels associated with the microbes in the plurality of microbes depicted in the final image.

VII. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A biological testing system comprising:
  (a) an incubator system, wherein the incubator system is configured to incubate a mixture disposed in a test well for an incubation period, wherein the mixture includes a plurality of microbes and an antimicrobial agent;
  (b) an optics system comprising
    a camera, wherein the camera is configured to capture raw images of the mixture; and
  (c) a processor, wherein the processor is configured to:
    (i) actuate the optics system to capture a raw image of the mixture in the test well;
    (ii) manipulate the raw image into a final image;
    (iii) count an amount of microbes in the final image;
    (iv) count an amount of pixels associated with the microbes in the final image;
    (v) determine a first ratio, wherein the first ratio is based at least in part on the relationship between the amount of microbes and the amount of pixels;
    (vi) wait for a time period;
    (vii) after the time period, repeat (i), (ii), (iii), (iv), and (v) to determine a second ratio; and
    (viii) determine a minimum inhibitory concentration of the antimicrobial agent with respect to the plurality of microbes based at least in part on the difference between the first ratio and the second ratio.

2. The biological testing system of claim 1, wherein optics system further comprises a stage, wherein the stage is configured to selectively receive the test well after incubating in the incubator system for the incubation period, wherein the camera is configured to selectively capture raw images of the mixture disposed in the test well on the stage.

3. The biological testing system of claim 1, further comprising a movement system configured to move the test well between the incubator system and the optics system.

4. The biological testing system of claim 1, wherein the processor is configured to:
  (a) prior to manipulating the raw image into the final image, determine the size of the microbes in the plurality of microbes depicted in the raw image; and
  (b) manipulate the raw image into the final image based at least in part on the size of the microbes.

5. The biological testing system of claim 1, wherein the processor is configured to:
  (a) enhance the raw image into an enhanced image; and
  (b) manipulate the enhanced image into the final image.

6. The biological testing system of claim 5, wherein the processor is configured to:
  (a) prior to enhancing the raw image into the enhanced image, determine the size of the microbes in the plurality of microbes depicted in the raw image; and
  (b) enhance the raw image into the enhanced image based at least in part on the size of the microbes.

7. The biological testing system of claim 1, further comprising a database, wherein the captured raw images are stored in the database.

8. A method comprising:
  (a) depositing a mixture into each test well in a test array, wherein the mixture in each test well includes a plurality of microbes and a differing concentration of an antimicrobial agent;
  (b) capturing a raw image of the mixture in each test well;
  (c) manipulating the raw image into a final image;
  (d) counting an amount of microbes in the final image;
  (e) counting an amount of pixels associated with the microbes in the final image;
  determining a first ratio, wherein the first ratio is based at least in part on the relationship between the amount of microbes and the amount of pixels;
  (g) waiting for a time period;
  (h) after the time period, repeating (b), (c), (d), (e), and (f) to determine a second ratio; and
  determining a minimum inhibitory concentration of the antimicrobial agent with respect to the plurality of microbes based at least in part on the difference between the first radio and the second ratio for each test well in the test array.

9. The method of claim 8, further comprising:
  (a) prior to manipulating the raw image into the final image, determining the size of the microbes in the plurality of microbes depicted in the raw image; and
  (b) manipulating the raw image into the final image based at least in part on the size of the microbes.

10. The method of claim 8, further comprising:
  (a) enhancing the raw image into an enhanced image; and
  (b) manipulating the enhanced image into the final image.

11. The method of claim 10, further comprising:
  (a) prior to enhancing the raw image into the enhanced image, determining the size of the microbes in the plurality of microbes depicted in the raw image; and
  (b) enhancing the raw image into the enhanced image based at least in part on the size of the microbes.

12. A method comprising:
  (a) depositing a mixture into each test well in a test array, wherein the mixture in each test well includes a plurality of microbes and a differing concentration of an antimicrobial agent;
  (b) capturing a raw image of the mixture in each test well;
  (c) manipulating the raw image into a final image;
  (d) determining a first morphology of the microbes in the final image;
  (e) waiting for a time period;
  (f) after the time period, repeating (b), (c), and (d) to determine a second morphology; and
  (g) determining a minimum inhibitory concentration of the antimicrobial agent with respect to the plurality of microbes based at least in part on the difference between the first morphology and the second morphology for each test well in the test array.

13. The method of claim 12, wherein one or both of the first morphology and the second morphology includes elongation of the microbes.

14. The method of claim 12, wherein one or both of the first morphology and the second morphology includes an abnormal growth in the size or shape of the microbes.

15. The method of claim 12, further comprising:
(a) prior to manipulating the raw image into the final image, determining the size of the microbes in the plurality of microbes depicted in the raw image; and
(b) manipulating the raw image into the final image based at least in part on the size of the microbes.

16. The method of claim 12, further comprising:
(a) enhancing the raw image into an enhanced image; and
(b) manipulating the enhanced image into the final image.

17. The method of claim 16, further comprising:
(a) prior to enhancing the raw image into the enhanced image, determining the size of the microbes in the plurality of microbes depicted in the raw image; and
(b) enhancing the raw image into the enhanced image based at least in part on the size of the microbes.

* * * * *